(12) United States Patent
Mazur et al.

(10) Patent No.: US 10,829,729 B2
(45) Date of Patent: Nov. 10, 2020

(54) CELLULAR PORATION USING LASER RADIATION

(71) Applicant: President and Fellows Of Harvard College, Cambridge, MA (US)

(72) Inventors: Eric Mazur, Concord, MA (US); Nabiha Saklayen, Cambridge, MA (US); Marinna Madrid, Cambridge, MA (US); Marinus Huber, Munich (DE); Valeria Nuzzo, Paris (FR)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/250,714

(22) Filed: Jan. 17, 2019

(65) Prior Publication Data
US 2019/0300834 A1 Oct. 3, 2019
US 2020/0010791 A9 Jan. 9, 2020

Related U.S. Application Data

(63) Continuation-in-part of application No. PCT/US2017/059743, filed on Nov. 2, 2017, and a
(Continued)

(51) Int. Cl.
C12N 15/87 (2006.01)
C12M 1/42 (2006.01)

(52) U.S. Cl.
CPC ............. C12M 35/02 (2013.01); C12N 15/87 (2013.01)

(58) Field of Classification Search
None
See application file for complete search history.

(56) References Cited

U.S. PATENT DOCUMENTS

| 5,013,668 A | 5/1991 | Fields |
| 9,551,648 B2 | 1/2017 | Ussembayev |

(Continued)

FOREIGN PATENT DOCUMENTS

| EP | 0137504 A2 | 4/1985 |
| EP | 2272945 A1 | 1/2011 |

(Continued)

OTHER PUBLICATIONS

Lukinaova-Hleb et al. Laser Pulse Duration Is Critical for the Generation of Plasmonic Nanobubbles (Langmuir, 2014, 30:7425-7434) (Year: 2014).*

(Continued)

*Primary Examiner* — Christopher M Babic
*Assistant Examiner* — Arthur S Leonard
(74) *Attorney, Agent, or Firm* — Nelson Mullins Riley & Scarborough LLP; Thomas J. Engellenner; Reza Mollaaghababa

(57) ABSTRACT

In one aspect, a method of cell processing is disclosed, which includes disposing a plurality of cells on a substrate across which a plurality of projections are distributed and an electrically conductive layer at least partially coating said projections, exposing the cells to a cargo to be internalized by the cells, irradiating the substrate surface (and in particular the projections) with continuous wave or pulsed laser radiation. For example, one or more laser pulses having a pulse width in a range of about 1 ns to about 1000 ns can be applied so as to facilitate uptake of the cargo by at least a portion of the cells (e.g., the cells positioned in the vicinity of the projections (e.g., within hundreds of nanometer (such as less than 100 nm) of the projections)). In some embodiments, the laser pulses have a pulse width in a range of about 10 ns to about 500 ns, e.g., in a range of about 5 ns to about 50 ns.

20 Claims, 29 Drawing Sheets

Related U.S. Application Data continuation-in-part of application No. PCT/US2017/059720, filed on Nov. 2, 2017.

(60) Provisional application No. 62/416,789, filed on Nov. 3, 2016, provisional application No. 62/442,293, filed on Jan. 4, 2017, provisional application No. 62/416,857, filed on Nov. 3, 2016.

(56) References Cited

U.S. PATENT DOCUMENTS

| | | | |
|---|---|---|---|
| 2007/0141163 A1 | 6/2007 | Vitaliano et al. | |
| 2010/0206380 A1 | 8/2010 | Lindquist | |
| 2012/0171746 A1 | 7/2012 | Mazur et al. | |
| 2013/0107254 A1 | 5/2013 | Yu et al. | |
| 2014/0315985 A1* | 10/2014 | May .................. | C12Q 1/68 514/44 R |
| 2018/0010149 A1 | 1/2018 | Mazur et al. | |

FOREIGN PATENT DOCUMENTS

| | | |
|---|---|---|
| WO | 2009017695 A1 | 2/2009 |
| WO | 2012158631 A2 | 11/2012 |
| WO | 2016127069 A1 | 8/2016 |

OTHER PUBLICATIONS

Lukianova-Hleb et al., Plasmonic Nanobubbles as Transient Vapor Nanobubbles Generated Around Plasmonic Nanoparticles. ACS Nano. Apr. 27, 2010; 4(4): 2109-2123. (Year: 2010).*

Baumgart et al., "Off-resonance plasmonic enhanced femtosecond laser optoporation and transfection of cancer cells," Biomaterials, Mar. 31, 2012 (Mar. 31, 2012), vol. 33, pp. 2345-2350.

Courvoisier et al., "Plasmonic Tipless Pyramid Arrays for Cell Poration," Nano Letters, Jun. 19, 2015 (Jun. 19, 2015), vol. 15, pp. 4461-4466.

Lukianova-Hleb et al., Selective gene transfection of individual cells in vitro with plasmonic nanobubbles. J Control Release. Jun. 10, 2011;152(2):286-293.

Yang et al., "Enhanced optical transmission mediated by localized plasmons in anisotropic three-dimensional nanohole arrays," Nano Letters. Jul. 16, 2010 (Mar. 31, 2012)., vol. 10, pp. 3173-3178.

Vogel et al., "A Convenient Method to Produce Close and NonClose-Packed Monolayers Using Direct Assembly at the Air-Water Interface and Subsequent Plasma-Induced Size Reduction," Macromolecular Chemistry and Physics. 2011, 212, 1719-1734 (Year: 2011).

International Search Report and Written Opinion received in PCT/US2016/016801 dated Apr. 15, 2016; 12 pages.

Nabiha Saklayen et al: "Intracellular Delivery Using Nanosecond-Laser Excitation of Large-Area Plasmonic Substrates", ACS Nano, vol. 11, No. 4, Apr. 1 25, 2017 (Apr. 25, 2017), pp. 3671-3680.

SeBastien Courvoisier et al: "Plasmonic Tipless Pyramid Arrays for Cell Poration", Nano Letters, vol. 15, No. 7, Jul. 8, 2015 (Jul. 8, 2015), pp. 4461-4466.

Eric Diebold: "Plasmon-enhanced nonlinear optics for applications in sensing and biology",Ph. A thesis, May 2010 (May 2010).

Ranhua Xiong et al: II Laser-assisted photoporation: fundamentals, technological advances and applications, Advances in Physics: X, vol. 1, No. 4, Jul. 3, 2016 (Jul. 3, 2016), pp. 596-620.

Yi-Chien Wu et al: "Massively parallel delivery of large cargo into mammalian cells with light pulses", Nature Methods, vol. 12, No. 5, May 2015 (May 2015), pp. 439-444.

Yi-Chien Wu et al: "Supplementary information.—Massively parallel delivery of large cargo into mammalian cells wit light pulses", Nature Methods, vol. 12, No. 5, Apr. 6, 2015 (Apr. 6, 2015), pp. 439-444.

Nabiha Saklayen et al: "Plasmonic Intracellular Delivery for Cell Therapy", Proceedings of Biomedical Optics Congress 2016, "Optics and the Brain 2016", Fortlauderdale, FL, USA,Jan. 2016 (Jan. 2016), p. CTh2A.3.

Sebastien Courvoisier et al: "Plasmonic Tipless Pyramid Arrays for Cell Poration", Nano Letters,vol. 15, No. 7, Jul. 8, 2015 (2015-87-08), pp. 4461-4466.

Nabiha Saklayen et al: "Analysis of poration-induced changes in cells from laser-activated plasmonic substrates" Biomedical Optics Express, vol. 8, No. 18, Oct. 1, 2017 (2017-18-81), p. 4756.

Mitsuhiro Tera Kawa et al: "Gene transfer into mammalian cells by use of a nanosecond pulsed laser-induced stress wave", Optics Letters, vol. 29, No. 11, Jun. 1, 2004 (Jun. 1, 2004), p. 1227.

Hans Georg Breunig et al: "High-throughput continuous flow femtosecond laser-assisted cell optoporation and transfection : Flow Cell Transfection", Microscopy Research and Technique, vol . 77, No. 12,Dec. 1, 2014 (Dec. 1, 2014), pp. 974-979.

International Search Report dated Apr. 19, 2018 from corresponding PCT/US2017/059743, pp. 7.

International Written Opinion dated Apr. 19, 2018 from corresponding PCT/US2017/059743, pp. 10.

International Search Report dated Mar. 28, 2018 from corresponding PCT/US2017/059720, pp. 7.

International Written Opinion dated Mar. 28, 2018 from corresponding PCT/US2017/059720, pp. 9.

Tognalli et al., From Single to Multiple Ag-Layer Modification of Au Nanocavity Substrates: A Tunable Probe of the ChemicalSurface-Enhanced Raman Scattering Mechanism, ACS Nano, 2011, 7:5433-5443 (Year 2011).

Kelf et al., Localized and delocalized plasmons in metallic nanovoids. Physical Review B 74, 245415, pp. 1-12, 2006 (Year:2006).

Perney et al., Tuning localized plasmons in nanostructured substrates for surface-enhanced Raman scattering. Optics Express vol. 14, Issue 2, pp. 847-857 (2006) (Year: 2006).

Coyle et al., Confined Plasmons in Metallic Nanocavities. (Phy Rev Lett, 2001, 87:1-4) (Year 2001).

Netti et al., Confined Surface Plasmons in Gold Photonic Nanocavities. Adv. Mater. 2001, 13, No. 18, Sep. 14, pp. 1368-1370 (Year 2001).

* cited by examiner

Dispose a plurality of cells and a cargo to be internalized by the cells to a surface of a cell-processing substrate having a plurality of metalized projections Apply one or more nanosecond laser pulses to said cells so as to facilitate uptake of the cargo by the cells

FIG. 1

| Sample ID | Final concentration of Au (parts per billion) |
|---|---|
| Control on glass | 20 |
| Gold nanoparticle control | 171 |
| B0 | 20 |
| G1 | 18 |
| G0R0 | 20 |
| E1 | 17 |
| E2 | 17 |
| E3 | 17 |

FIG. 16

| Probe | Fluorochrome | Vendor/ Cat. No. |
|---|---|---|
| Calcein green | FITC | ThermoFisher Scientific/ C481 |
| FITC-dextran 10 kDa | FITC | Sigma-Aldrich/ FD10S |
| FITC-dextran 70 kDa | FITC | Sigma-Aldrich/ FD70S |
| FITC-dextran 150 kDa | FITC | Sigma-Aldrich/ FD150S |
| FITC-dextran 500 kDa | FITC | Sigma-Aldrich/ FD500s |
| FITC-dextran 2000 kDa | FITC | Sigma-Aldrich/ FD2000S |
| Live-dead discriminator | CellTrace Calcein red-orange, AM (PE channel in flow cytometer) | ThermoFisher Scientific/ C34851 |
| BD CS&T beads used for QC | BD™ Cytometer Setup & Tracking Beads (used with FACSDiva software v 6.x) | BD Biosciences Catalog #: 642412 |

FIG. 17

| Sample ID | Description | Laser scanned | FITC channel | Calcein red-orange AM channel |
|---|---|---|---|---|
| B0 | Control: blank sample to set initial gates. | No | No | No |
| G0R0 | Control: to determine background of green dye and viability of cells when not laser scanned. | No | Yes | Yes |
| G1 | Control: negative control for viability. | Yes | Yes | No |
| E1-E3 | Experiments: in triplicate. | Yes | Yes | Yes |

FIG. 18

| Laser | Parameter name | Long pass filter | Bandpass filter |
|---|---|---|---|
| 488 nm | SSC | n/a | 400/10 |
| 488 nm | FITC-Cargo | 505 | 530/30 |
| 561 nm | Calcein AM red-orange | n/a | 582/15 |
| *FSC detector is a photodiode | | | |

FIG. 19

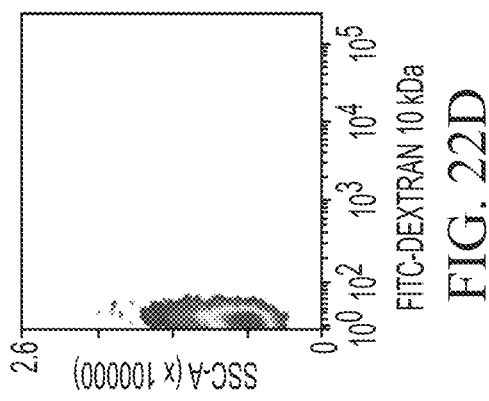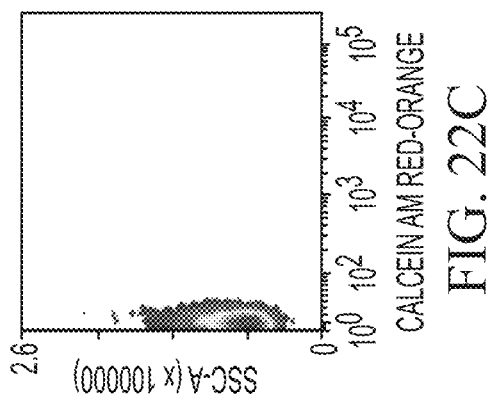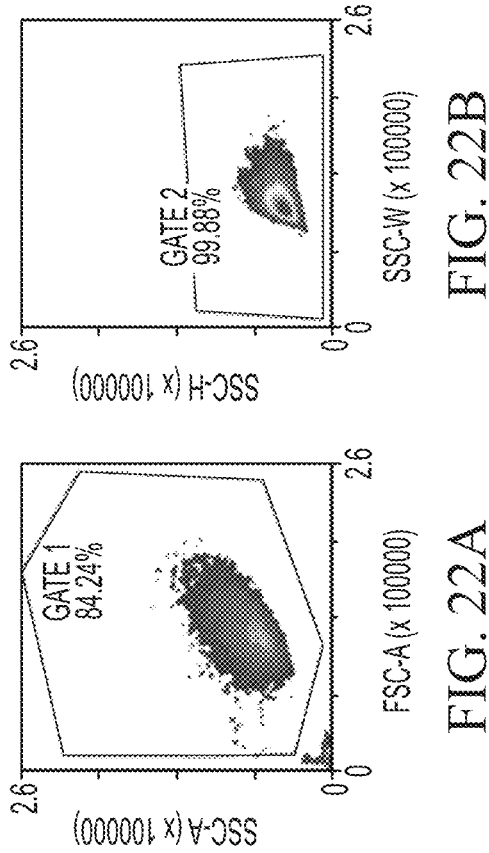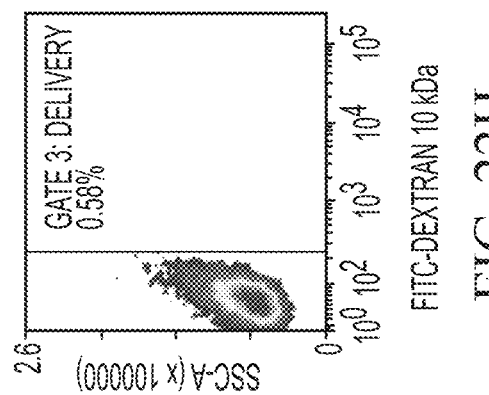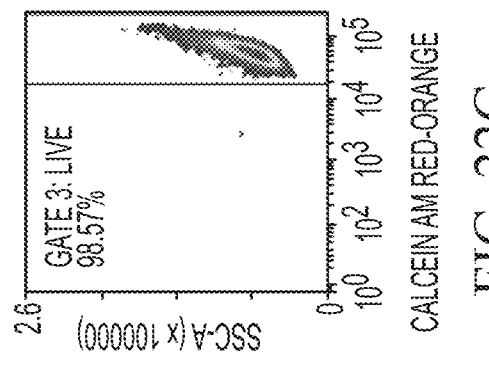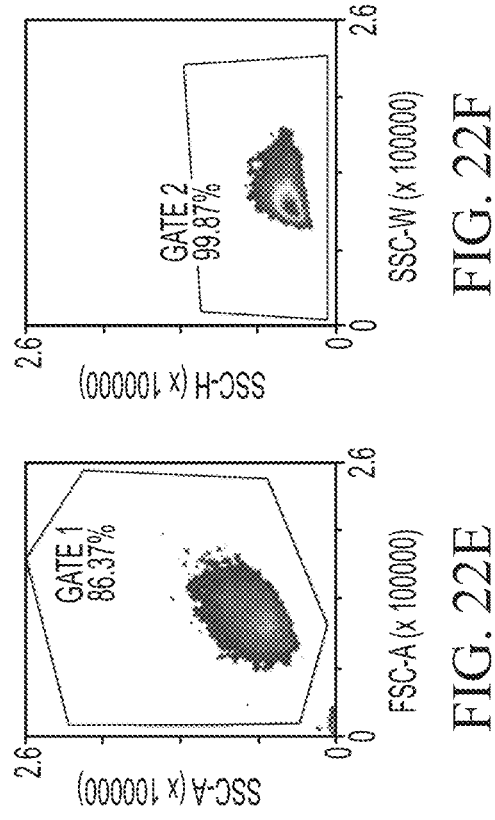

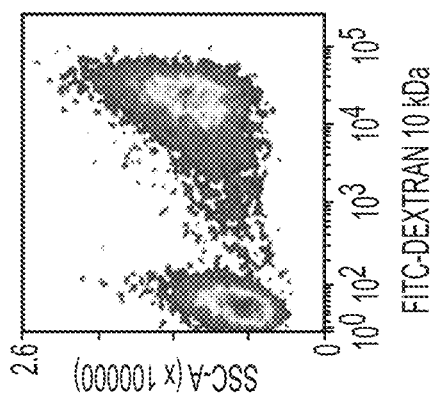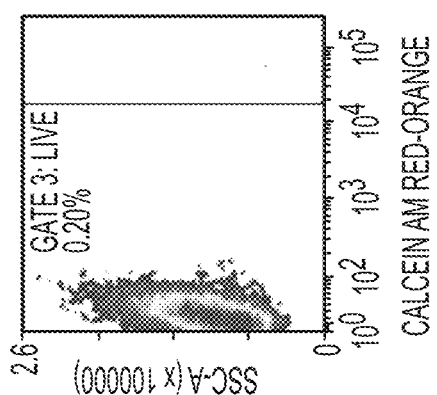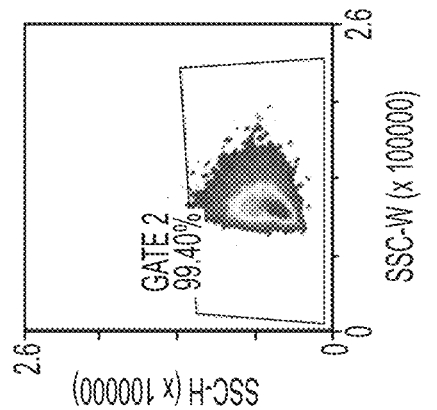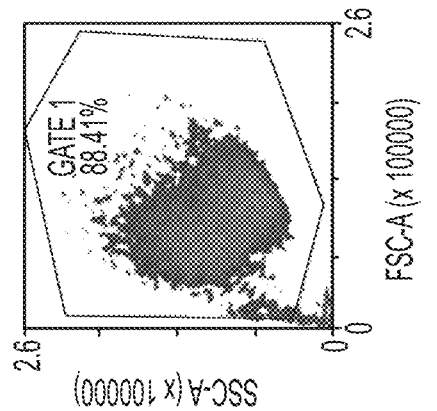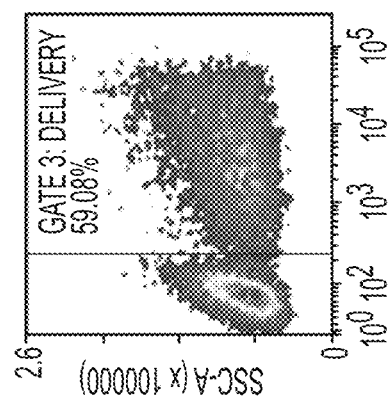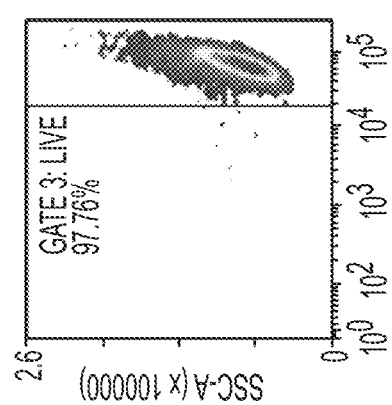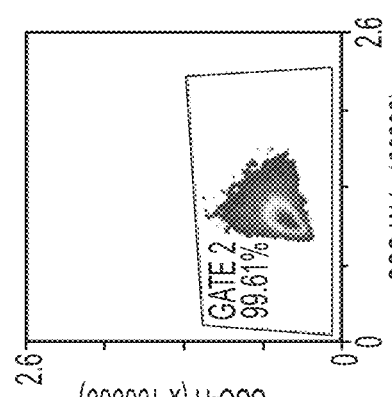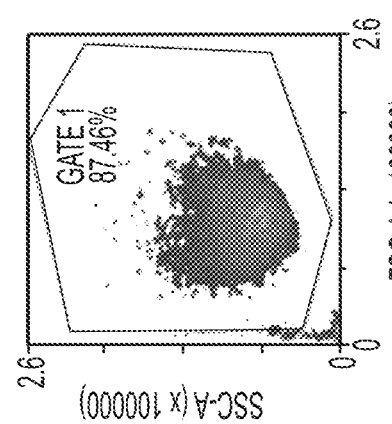
FIG. 22I  FIG. 22J  FIG. 22K  FIG. 22L
FIG. 22M  FIG. 22N  FIG. 22O  FIG. 22P

CELLULAR PORATION USING LASER RADIATION

CROSS-REFERENCE TO RELATED APPLICATIONS

The present application is a Continuation-In-Part Application of International Application No. PCT/US2017/059720, filed Nov. 2, 2017, which claims the benefit of U.S. Provisional Application No. 62/416,857, filed Nov. 3, 2016. The present application also is a Continuation-In-Part Application of International Application No. PCT/US2017/059743, filed Nov. 2, 2017, which claims the benefit of U.S. Provisional Application No. 62/416,789, filed Nov. 3, 2016 and U.S. Provisional Application No. 62/442,293, filed Jan. 4, 2017 789. The disclosures of each of the above patent applications is hereby incorporated by reference in its entirety.

STATEMENT OF GOVERNMENT SUPPORT

The present invention was made with United States government support under Grant Nos. PHY 1219334 and PHY-1205465 from the National Science Foundation. The United States government has certain rights in this invention.

FIELD

This disclosure relates generally to substrates and methods for delivery of cargos to cells. More particularly, in some aspects, the present teachings relate to cellular poration and intracellular cargo delivery methods using laser radiation and thermoplasmonic substrates.

BACKGROUND

The direct intracellular delivery of biological and non-biological materials is a powerful way to manipulate cell behavior for a wide range of applications. For example, functional proteins are delivered to ablate genes in hematopoietic stem cells with high precision for research and therapeutic applications. Enzymes are delivered for their ability to bind targets with high affinity and specificity and siRNA delivery has created opportunities in gene silencing for biomedical applications. In the case of blood disorders such as human immunodeficiency virus (HIV) or leukemia, delivering functional molecules into a patient's stem cells for transplantation therapy shows promise for curing such disorders, circumventing the side effects of chemotherapy and the search for a matching donor.

The ability to effectively deliver large and diverse cargos such as, without limitation, amino acids, peptides, proteins, protein cages, antibodies, polysaccharides, nucleic acids, viruses, or DNAs/RNAs directly into cells would be a huge boost for biomedical research. However, no current intracellular delivery method, either biological, chemical or physical, can offer all desirable "high-performance" features for intracellular delivery at once: (1) high efficiency, viability, and throughput, (2) diverse cargo delivery capability, (3) spatial selectivity (delivering to specific cells disposed on a surface), scalability and reproducibility, (4) no post-delivery immunotoxicity, and (5) cost-effectiveness.

Viral transduction is the most popular biological method due to decades of extensive research, but has limitations. For example, viral methods offer limited cargo-carrying capacity, only deliver genetic cargo, and include immunotoxicity risks.

Accordingly, there is a need for enhanced substrates and methods for intracellular delivery of diverse cargos into cells.

SUMMARY

In one aspect, a method of cell processing is disclosed, which includes disposing a plurality of cells on a substrate across which a plurality of projections are distributed and an electrically conductive layer at least partially coating said projections, exposing the cells to a cargo to be internalized by the cells, irradiating the substrate surface (and in particular the projections) with continuous or pulsed radiation.

When continuous radiation is applied, the radiation can have a wavelength in a range of about 200 nm to about 5 microns, and an intensity in a range of about $10^2$ W/cm$^2$ to about $10^5$ W/cm$^2$, or in a range of about $10^3$ W/cm$^2$ to about $10^4$ W/cm$^2$. By way of example, in some embodiments, a laser intensity of at least about $10^4$ W/cm$^2$ can be used for delivery of a cargo into one or more cells. It has been unexpectedly discovered that even at such high intensities and fluences, many of the processed cells survive and divide. The continuous laser radiation can be applied to the substrate for a time duration of at least about 1 ms, e.g., for a time duration in a range of about 1 ms to about 500 ms.

When pulsed radiation is employed, one or more laser pulses having a pulse width in a range of about 1 ns to about 1000 ns can be applied so as to facilitate uptake of the cargo by at least a portion of the cells (e.g., the cells positioned in the vicinity of the projections (e.g., within hundreds of nanometer (such as less than a few hundred nanometers (e.g., less than about 1000 nm) of the projections). In some embodiments, the laser pulses have a pulse width in a range of about 10 ns to about 500 ns, e.g., in a range of about 20 ns to about 100 ns.

In some embodiments, the laser pulses are applied to the cells at a fluence in a range of about 0.01 mJ/cm$^2$ to about 1000 mJ/cm$^2$, e.g., in a range of about 40 mJ/cm$^2$ to about 90 mJ/cm$^2$, or in a range of about 50 mJ/cm$^2$ to about 80 mJ/cm$^2$.

In some embodiments, the laser pulses are applied to the cells with a repetition rate in a range of about 0.1 Hz to about 100 GHz, e.g., in a range of about 1 Hz to about 100 Hz.

In another aspect, the present invention provides methods of cell processing, which include disposing at least one cell on or near a structured metal surface, exposing the cell to at least an external cargo, and irradiating the metal surface with a continuous laser radiation at an intensity in a range of about $10^2$ W/cm$^2$ to about $10^5$ W/cm$^2$ so as to facilitate uptake of the cargo by the cell. By way of example, the metal surface can be irradiated for at least about 1 ms. In some embodiments, the structured metal surface includes a plurality of metalized projections, e.g., metalized pyramids. In some such embodiments, upon irradiation of the metalized pyramids, at least some of the cells in proximity of the pyramids (e.g., cells positioned within hundreds of nanometers (e.g., 1000 nm)) can undergo a physical and/or chemical change, which can facilitate uptake of a cargo by those cells.

In some embodiments, the electrically conductive layer has a thickness in a range of about 1 nm to about 1 micron, e.g., in a range of about 20 nm to about 100 nm or in a range of about 10 nm to about 50 nm. The conductive layer can be formed of a plurality of different materials, such as gold, silver, copper, metallic titanium oxide, titanium, titanium nitride, platinum, palladium, chromium, among others.

In some embodiments, the electrically conductive coating has a substantially uniform thickness across the substrate. In some embodiments, the conductive coating continuously covers the projections and the surface portions between the projections.

In some embodiments, the projections are distributed across the substrate surface as a regular array, e.g., a regular two-dimensional array. For example, the projections can form a two dimensional lattice, such as a hexagonal lattice. In some such embodiments, the projections are separated from one another by a spacing in a range of about 1 nm to about 500 µm, e.g., in a range of about 0.1 µm to about 100 µm or in a range of about 1 µm to about 50 µm or in a range of about 10 µm to about 30 µm.

In some embodiments, the projections have a substantially uniform height. In some embodiments, the projections are a plurality of pyramids. In some such embodiments, the pyramids have a height, e.g., in a range of about 0.1 µm to about 20 µm, or a range of about 1 µm to about 10 µm. Further, in some such embodiments, the pyramids have a base length, e.g., in a range of about 0.1 µm to about 100 µm, or in a range of about 1 µm to about 10 µm. In many embodiments, the pyramids can have substantially uniform heights and base lengths. In some embodiments, the pyramids are distributed across the substrate surface as a regular array (e.g., as a regular two-dimensional array). In some such embodiments, the pyramids are spaced from one another by a spacing in a range of about 1 nm to about 500 µm, e.g., in a range of about 0.1 µm to about 100 µm, or in a range of about 1 µm to about 10 µm.

In some embodiments, the applied laser radiation can cause a transient change in the cells sufficient to allow the uptake of one or more cargos in vicinity of the cells. By way of example, such a transient change can be a change in the permeability of the cell's membrane.

In some embodiments, the substrate comprises a polymer. Some examples of such polymers include, without limitation, polymethyl methacrylate, mercapto-ester, epoxy glue, UV glue, and polydimethylsiloxane. In some embodiments, the substrate can be a semiconductor substrate (e.g., silicon, sapphire, and diamond). In some embodiments, the substrate can be formed of glass. In some embodiments, the introduction of a cargo into a plurality of cells can be achieved at an efficiency of at least about 40%, or at least about 50%, or at least about 60%, or at least about 70%, or at least about 80%, or at least about 90%, e.g., in a range about 85% to about 95%. Further, in some embodiments, the processed cells can exhibit a cell viability of at least about 70%, or at least about 80%, or at least about 90%, or at least about 95%, e.g., about 98% or greater.

In some embodiments, the introduction of a cargo into the processed cells can be achieved at a rate of at least about 10,000 cells/min, or at least about 20,000 cells/min, or at least about 30,000 cells/min, or at least about 40,000 cells/min, or at least about 50,000 cells/min, or at least about 100,000 cells/min, or at least 500,000 cells/min, or at least 1 million cells/min, or at least 10 million cell/min, or at least 100 million cells/min.

A variety of different cargos can be delivered to cells using the substrates and the methods discussed herein. By way of example, the cargo can be a macromolecule. In some embodiments, the cargo can be any of a deoxyribonucleic acid (DNA), a ribonucleic acid (RNA), a plasmid, a protein, a dye, a polymer, a quantum dot, a nanoparticle, a protein, a protein complex, and a polysaccharide. In some embodiments, a Cas9/gRNA protein complex can be delivered to cells.

Further, the methods and substrates according to the present teachings can be employed to deliver cargos to a variety of different cell types. Some examples of cell types include, without limitation, an epithelial cell, a neuron, a fibroblast, a stem cell, an immune cell (e.g., a T cell), and a blood cell. In some embodiments, the cells can be mammalian cells.

In some embodiments, the application of the continuous or pulsed laser radiation to a metalized surface projection can cause a rise in temperature of at least a portion thereof. By way of example, such a temperature rise can be at least about 275° C., e.g., in a range of about 275° C. to about 500° C. In some embodiments in which the projections are in the form of a plurality of pyramids, the temperature rise is more pronounced in the vicinity of the tips of the pyramids.

In some embodiments, the cells and one or more cargos to be internalized by the cells are disposed in a liquid medium, e.g., a water-based medium, and the medium is applied to the substrate surface. In some such embodiments, the application of the continuous or pulsed laser radiation to the substrate can cause an increase in the temperatures of the projections (e.g., the pyramids), e.g., due to plasmonic excitation in the metal layer coating the projections. In some cases, the temperature rise can be sufficient to cause formation of bubbles and/or pressure waves in the medium and around the cell membrane, which can in turn cause a change in the permeability of the cells, thus facilitating the uptake of nearby cargo(s) by the cells.

In a related aspect, a cell-processing substrate (herein also referred to as a thermoplasmonic substrate) is disclosed, which includes a substrate having a plurality of projections distributed across a surface thereof, and an electrically conductive layer at least partially covering the projections. In some embodiments, the projections have a substantially uniform height. Further, in some embodiments, the conductive layer has a substantially uniform thickness.

In some embodiments, the projections have a pyramidal shape extending from a base to an apex. In some such embodiments, the pyramids have a height, e.g., in a range of about 0.1 µm to about 20 µm, or a range of about 1 µm to about 10 µm. Further, in some such embodiments, the pyramids have a base length, e.g., in a range of about 0.1 µm to about 100 µm, or in a range of about 1 µm to about 10 µm. In many embodiments, the pyramids can have substantially uniform heights and base lengths. In some embodiments, the electrically conductive layer has a thickness in a range of about 1 nm to about 100 nm. In some embodiments, the conductive layer has a substantially uniform thickness across the substrate surface. In some such embodiments, the conductive layer provides a uniform coating that substantially covers the entire substrate surface including the surfaces of the projections. The electrically conductive layer can be formed of a variety of different materials, such as a variety of different metals. Some examples of suitable conductive materials include, for example, silver, gold, copper and metallic titanium nitride.

In another aspect, a cartridge is disclosed, which includes a cell-processing substrate having a metalized surface and an opposed back surface, a polymeric layer disposed in proximity of said metalized surface and separated therefrom by a gap to allow introduction of a sample onto the metalized surface. In some embodiments, the cartridge can include another polymeric layer disposed in proximity of the back surface of the cell-processing substrate. By way of example, each of the polymeric layers can include any of poly(methyl) methacrylate (PMMA) and polydimethylsiloxane (PDMS).

In a related aspect, a system for cell processing is disclosed, which includes a cartridge including a cell-processing substrate having a metalized surface comprising a plurality of projections at least partially coated with an electrically conductive coating, and a device for receiving said cartridge and exposing said metalized surface to laser radiation.

In some embodiments of the above system, the device can include an enclosure for receiving the cartridge. Further, the device can include a laser for generating laser radiation and a radiation scanning system for receiving the laser radiation and scanning the radiation over the metalized surface of the cartridge.

Further understanding of various aspects of the invention can be obtained by reference to the following detailed description in conjunction with the associated drawings, which are described briefly below.

BRIEF DESCRIPTION OF THE DRAWINGS

The present disclosure is described with reference to the following figures, which are presented for the purpose of illustration only and are not intended to be limiting.

In the Drawings:

FIG. 1 is a flow chart depicting various steps in an exemplary embodiment for delivering cargos to cells in accordance with aspects of the present disclosure;

FIG. 16 is a table presenting ICP-MS experimental information for Dextran 10 kDa delivery in accordance with aspects of the present disclosure;

FIG. 17 is a table depicting the reagent list for flow cytometry experiments;

FIG. 18 is a table depicting sample information for flow cytometry data sets;

FIG. 19 is a table depicting flow cytometry settings on BD LSRFortessaSORP™ cell analyser running BD FACSDiva software version 6.1.3;

FIG. 22A is a flow cytometry diagram depicting FSC-A as a function of SSC-A of a control blank sample to set initial gates in accordance with aspects of the present disclosure;

FIG. 22B is a flow cytometry diagram depicting SSC-W as a function of SSC-H of a control blank sample to set initial gates in accordance with aspects of the present disclosure;

FIG. 22C is a flow cytometry diagram depicting calcein AM red-orange fluorescence as a function of SSC-A of a control blank sample to set initial gates in accordance with aspects of the present disclosure;

FIG. 22D is a flow cytometry diagram depicting FITC-Dextran 10 kDa fluorescence as a function of SSC-A of a control blank sample to set initial gates in accordance with aspects of the present disclosure;

FIG. 22E is a flow cytometry diagram depicting FSC-A as a function of SSC-A of control sample to determine background of green dye and viability of cells when not laser scanned in accordance with aspects of the present disclosure;

FIG. 22F is a flow cytometry diagram depicting SSC-W as a function of SSC-H of control sample to determine background of green dye and viability of cells when not laser scanned in accordance with aspects of the present disclosure;

FIG. 22G is a flow cytometry diagram depicting calcein AM red-orange fluorescence as a function of SSC-A of a control sample to determine background of green dye and viability of cells when not laser scanned in accordance with aspects of the present disclosure;

FIG. 22H is a flow cytometry diagram depicting FITC-Dextran 10 kDa fluorescence as a function of SSC-A of a control sample to determine background of green dye and viability of cells when not laser scanned in accordance with aspects of the present disclosure;

FIG. 22I is a flow cytometry diagram depicting FSC-A as a function of SSC-A of a negative control sample for viability in accordance with aspects of the present disclosure;

FIG. 22J is a flow cytometry diagram depicting SSC-W as a function of SSC-H of a negative control sample for viability in accordance with aspects of the present disclosure;

FIG. 22K is a flow cytometry diagram depicting calcein AM red-orange fluorescence as a function of SSC-A of a negative control sample for viability in accordance with aspects of the present disclosure;

FIG. 22L is a flow cytometry diagram depicting FITC-Dextran 10 kDa fluorescence as a function of SSC-A of a negative control sample for viability in accordance with aspects of the present disclosure;

FIG. 22M is a flow cytometry diagram depicting FSC-A as a function of SSC-A of experimental sample in accordance with aspects of the present disclosure;

FIG. 22N is a flow cytometry diagram depicting SSC-W as a function of SSC-H of experimental sample in accordance with aspects of the present disclosure;

FIG. 22O is a flow cytometry diagram depicting calcein AM red-orange fluorescence as a function of SSC-A of experimental sample in accordance with aspects of the present disclosure;

FIG. 22P is a flow cytometry diagram depicting FITC-Dextran 10 kDa fluorescence as a function of SSC-A of experimental sample in accordance with aspects of the present disclosure;

Figure 23A:
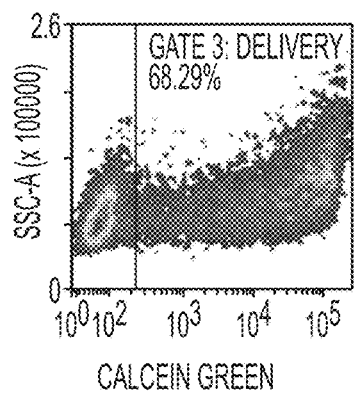
FIG. 23A is a flow cytometry diagram depicting calcein green fluorescence as a function of SSC-A in accordance with aspects of the present disclosure.
Figure 23B:
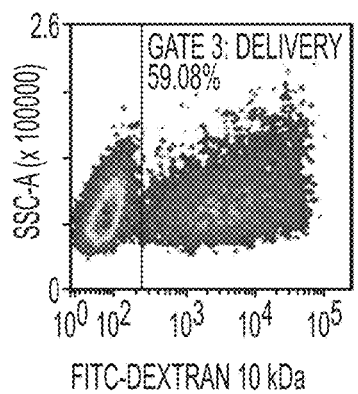
FIG. 23B is a flow cytometry diagram depicting FITC-dextran 10 kDa fluorescence as a function of SSC-A in accordance with aspects of the present disclosure.
Figure 23C:
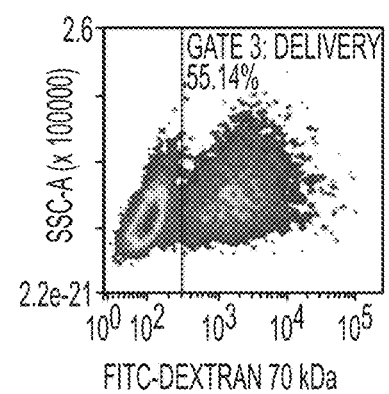
Figure 23D:
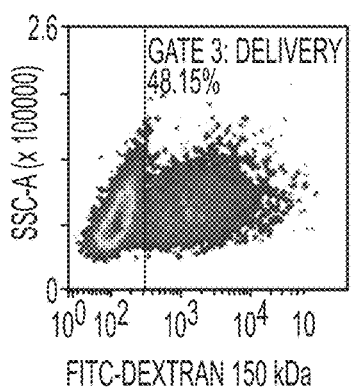
Figure 23E:
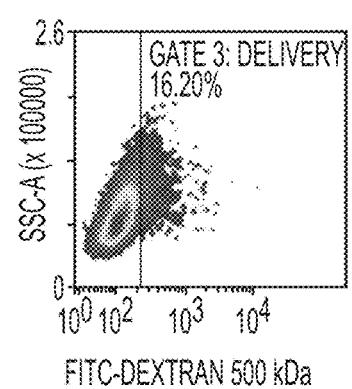
Figure 23F:
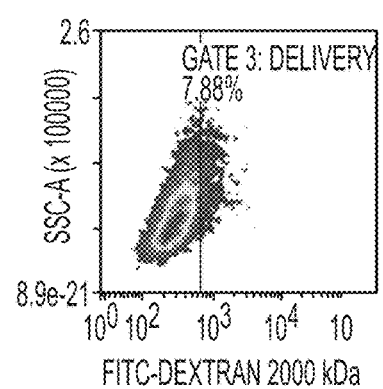
Figure 24:
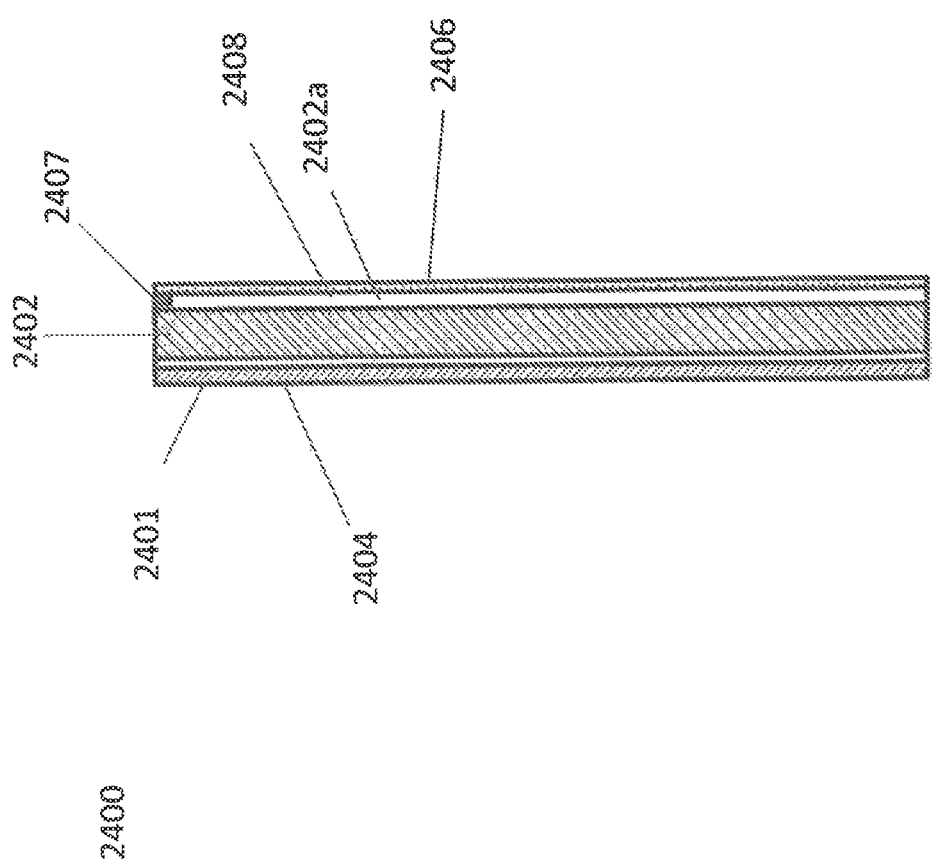
Figure 25A:
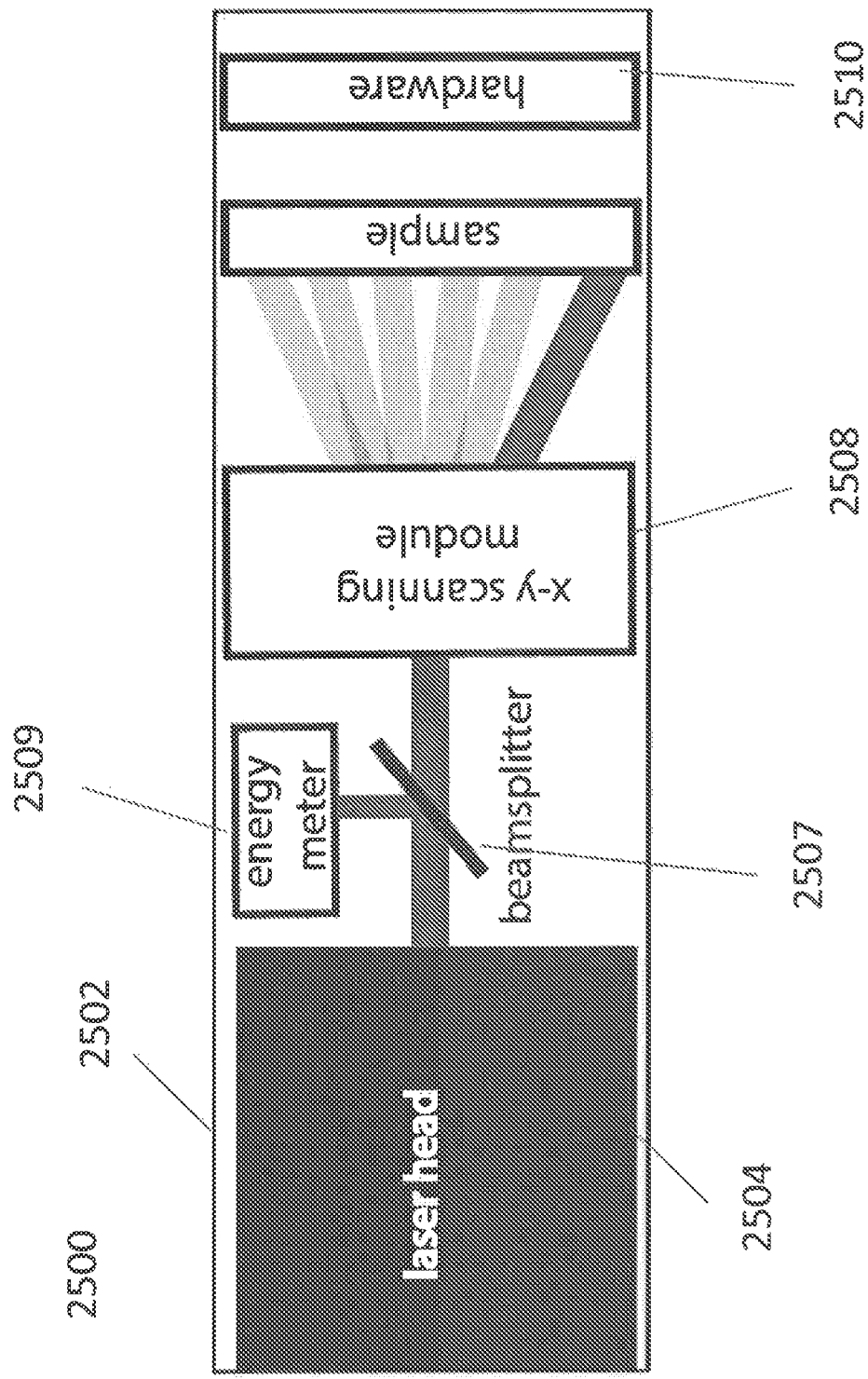
Figure 25B:
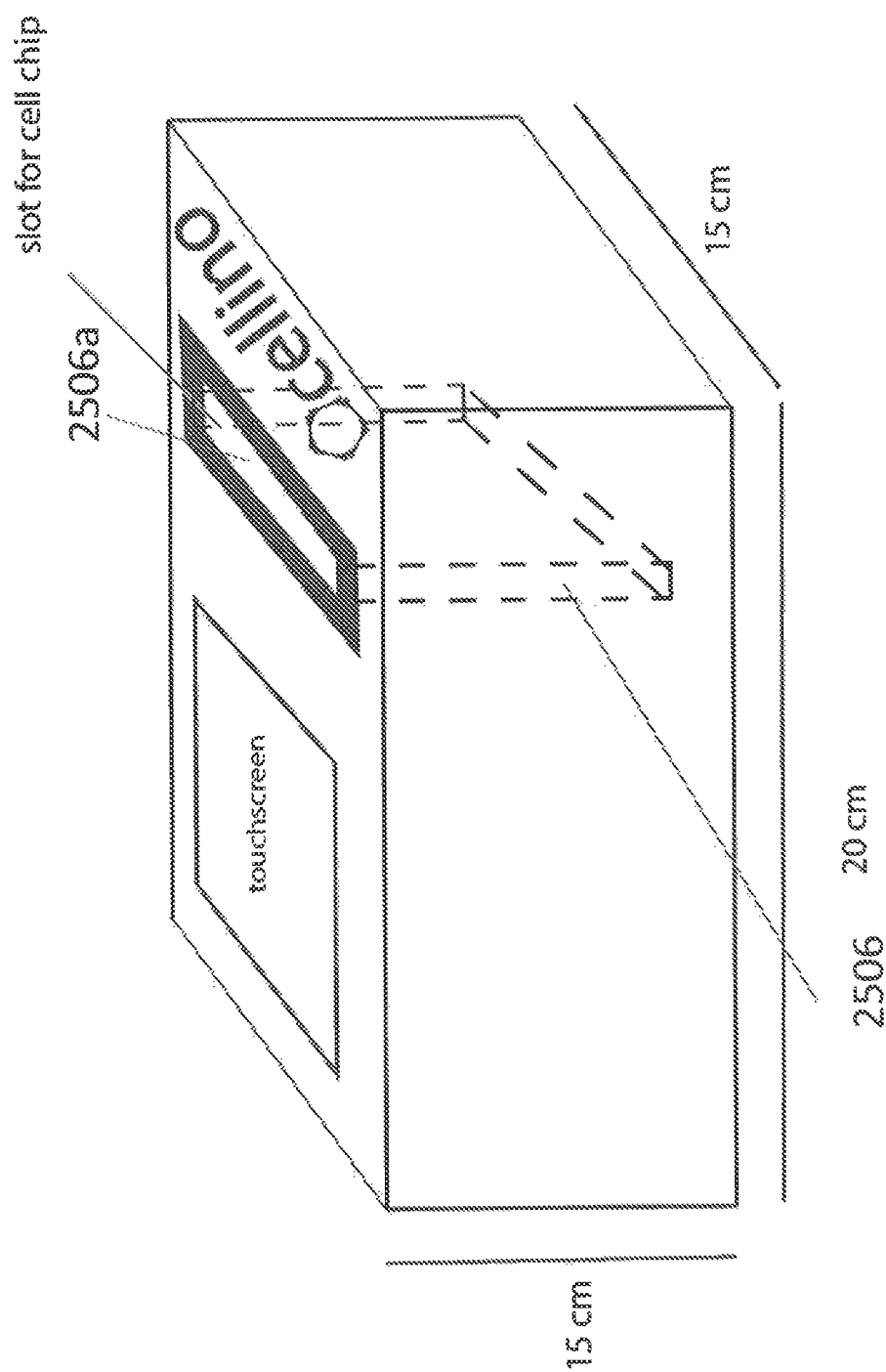
Figure 26:
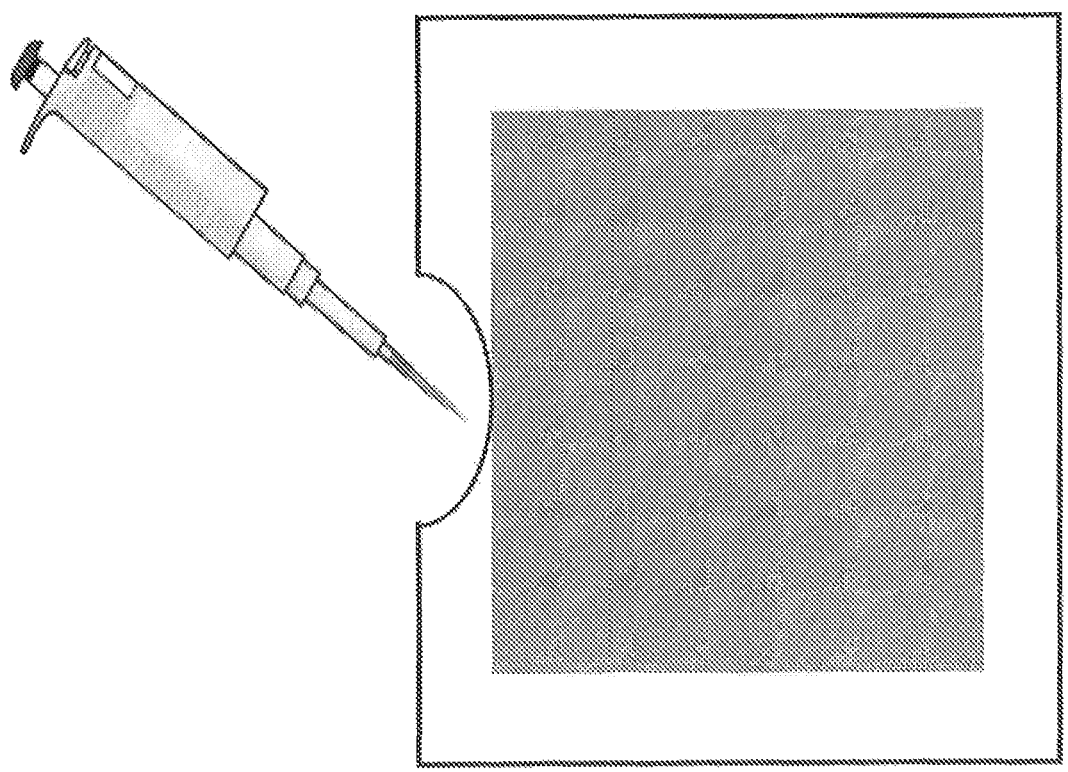

FIB. 23C is a flow cytometry diagram depicting FITC-dextran 70 kDa fluorescence as a function of SSC-A in accordance with aspects of the present disclosure;

FIG. 23D is a flow cytometry diagram depicting FITC-dextran 150 kDa fluorescence as a function of SSC-A in accordance with aspects of the present disclosure;

FIG. 23E is a flow cytometry diagram depicting FITC-dextran 500 kDa fluorescence as a function of SSC-A in accordance with aspects of the present disclosure;

FIG. 23F is a flow cytometry diagram depicting FITC-dextran 2000 kDa fluorescence as a function of SSC-A in accordance with aspects of the present disclosure;

FIG. 24 schematically depicts a cartridge according to an embodiment, which includes a thermoplasmonic substrate according to the present teachings;

FIG. 25A is a top schematic view of a device according to an embodiment of the present teachings, which can receive the cartridge shown in FIG. 24 and expose its metalized surface to laser radiation;

FIG. 25B is a perspective schematic view of the device depicted in FIG. 25A;

FIG. 26 schematically depicts the introduction of a sample, e.g., a sample containing cell, into the cartridge depicted in FIG. 24.

DETAILED DESCRIPTION

The present disclosure relates generally to substrates for use in processing cells and method of cells processing that allow causing changes in cells that facilitate uptake of cargos by the cells. As discussed in more detail below, in some embodiments, a medium containing one or more cells and one or more cargos to be internalized by the cells is disposed on a substrate surface having a plurality of metalized projections. The application of continuous wave radiation or a plurality of laser pulses to the cells can mediate the uptake of the cargo(s) by the cells. It has been discovered that the use of nanosecond pulses in combination with a substrate having metalized projections as discussed herein leads to efficient introduction of many types of cargos into cells at a high cell viability. In some embodiments, the substrates and the methods of the invention allow for the direct delivery of functional cargo to millions of cells on a minute timescale (e.g., at a rate of at least about 50,000 cells/min). Such a high throughput processing of cells can find applications in a variety of different areas, such as gene therapy, drug discovery, high-throughput screening, and the study of cellular function. As discussed in more detail below, a variety of different cargos can be delivered to cells using the substrates and the methods of the invention. By way of example, cargos having molecular weights in a range of about 0.6 to 2000 KDa can be delivered to cells with a high efficiency (e.g., as high as 95%), a high viability (e.g., 98%). Without being limited to any particular theory, in some embodiments, the application of laser radiation to the substrate can cause heating of the projections, particularly at their tips, which can in turn cause formation of bubbles and/or pressure waves in the medium in which the cells are entrained. In some cases, such bubbles can cause formation of transient pores in the cells' membranes, which can in turn facilitate the uptake of the cargo(s) by the cells.

Various terms are used herein consistent with their common meanings in the art. The following terms are defined below for clarity.

The term "polymer" is used herein consistent with its common meaning in the art to refer to a macromolecule formed by the chemical union of five or more repeating chemical units, e.g., by repeating monomers.

The term "cargo" and "agent" as used herein refer to any compound, molecule, molecular complex, and/or biological organisms, such as plasmid or viruses.

The term "thermoplasmonic" is used herein to refer to the behavior of metallic structures, such as nano-sized structures, that act as heaters by absorbing light energy and converting that energy into heat.

The efficiency of uptake of a cargo by a plurality of cells refers to the percentage of cells that contain the cargo after undergoing thermoplasmonic intracellular delivery according to the present teachings.

The cell viability as used herein refers to the percentage of cells that survive after undergoing thermoplasmonic intracellular delivery according to the present teachings.

The term "about" as used herein denotes a variation of at most 10% around a numerical value.

The term "substantially" denotes a deviation of at most 5% relative to a complete state and/or condition.

The term "nanosecond pulse(s)" refers to radiation pulse (s) having a pulse width in a range of about 1 nanosecond to about 1000 nanoseconds, e.g., in a range of about 1 nanosecond to about 500 nanoseconds.

Figure 2:
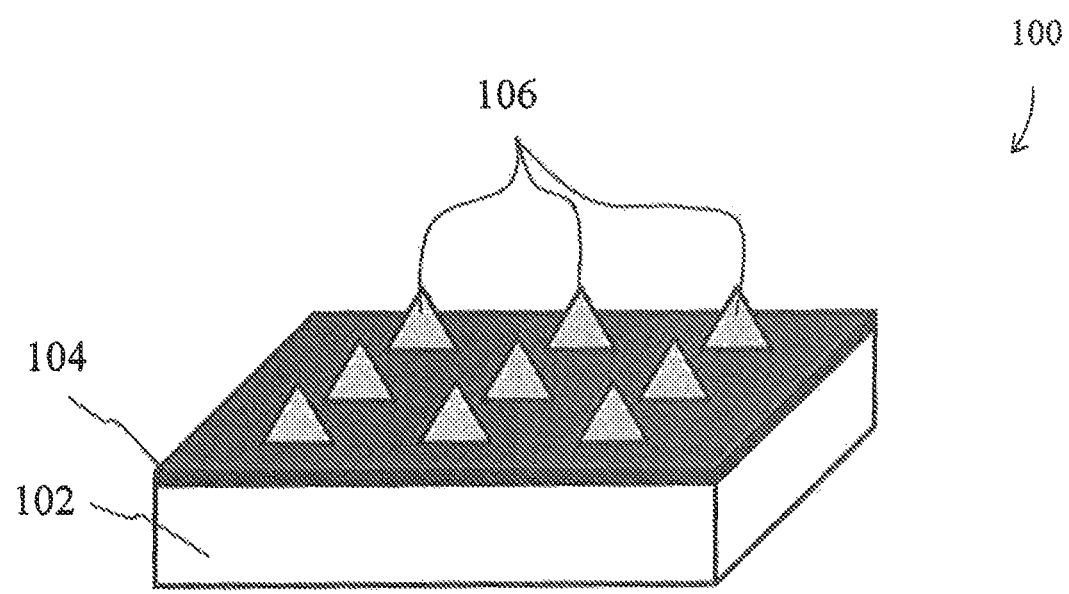
FIG. 2 is a schematic representation of a perspective view of a cell-processing structure in accordance with an embodiment of the present disclosure.
Figure 3:
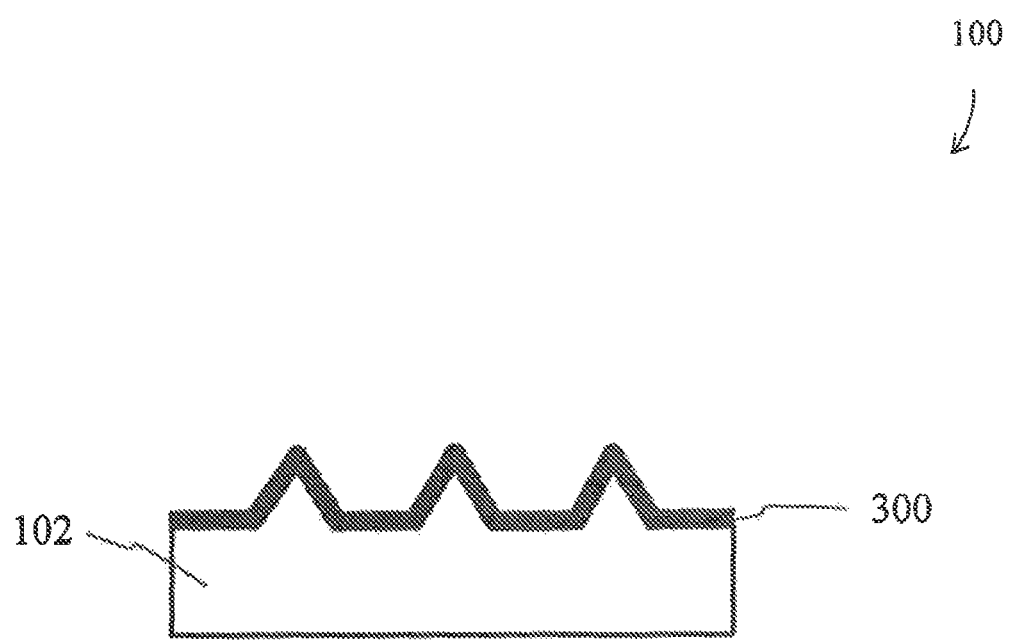
FIG. 3 is a schematic representation of a front view of a cell-processing structure in accordance with an embodiment of the present disclosure.

With reference to flow chart of FIG. 1 as well as FIGS. 2 and 3, in a method of processing cells according to an embodiment of the present teachings, one or more cells can be disposed on a metalized surface 100a of a cell-processing structure 100 (herein also referred to as a thermoplasmonic or cell-processing substrate) in presence of at least one cargo (herein also referred to as agent), such as a biological agent, and irradiated with one or more laser radiation pulses having a pulse width in a range of about 1 nanosecond to 1000 nanoseconds, e.g., in a range of about 1 nanosecond to about 500 nanoseconds, or in a range of about 20 nanoseconds to about 100 nanoseconds, or in a range of about 10 nanoseconds to about 50 nanoseconds so as to cause a transformation in cell(s) that facilitates the uptake of the agent by the cells. By way of example, the transformation caused by the applied laser pulses can be a transient change in the permeability of the cells' membranes, which allows the passage of the agent into the cells.

Figure 4:
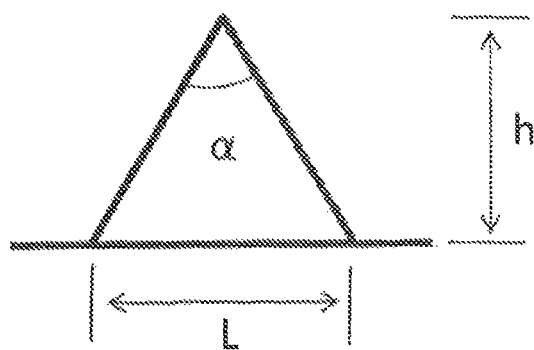
FIG. 4 is a schematic representation of a pyramid of a cell-processing structure in accordance with an embodiment of the present disclosure.

More specifically, the cell-processing substrate 100 includes a support substrate 102 having a top surface 104 across which a plurality projections 106 in the form of pyramids are distributed. In this embodiment, the pyramids 106 are distributed across the surface of the substrate 102 as a regular two-dimensional array. In other embodiments, the pyramids 106 may be randomly distributed across the substrate surface. In some embodiments, the pyramids can have a height (H) in a range of about 0.1 µm to about 20 µm, or a range of about 1 µm to about 10 µm. Further, in some embodiments, pyramidal surfaces can form an angle (α) of about 70.6 degrees relative to one another, as shown schematically in FIG. 4. In this embodiment, the pyramids 106 have a square base characterized by four equal sides having a size in a range of about 10 nm to about 500 µm, e.g., in a range of about 100 nm to 10 µm or in a range of about 100 µm to 400 µm. In other embodiments, the pyramids 106 can have triangular bases. In some embodiments, the spacing between neighboring pyramids can be, for example, in a range of about 1 nm to about 500 µm. In some embodiments, the surface density of the pyramids (i.e., the number of pyramids per unit area of the substrate surface across which the pyramids are distributed) can be in a range of about 1 million/cm$^2$ to about 100 millions/cm$^2$, e.g., in a range of about 10 millions/cm$^2$ to about 100 millions/cm$^2$, or in a range of about 20 millions/cm$^2$ to about 100 millions/cm$^2$.

With continued reference to FIG. 3, in this embodiment, a thin electrical conductive layer 300, such as a thin metal layer, coats the top surface of the substrate including the exposed pyramidal surfaces. In some embodiments, the thickness of the metal layer can be, for example, in a range of about 1 nm to about 100 nm. A variety of metals can be used to form the metal layer 300. Some suitable examples include gold, silver, and copper. In some embodiments, the coating 300 can be formed of TiN. The substrate 102 can also be formed of a variety of different materials. In this embodiment, the substrate 102 is formed of a polymeric material. Some examples of suitable polymeric materials include, without limitation, polymethyl methacrylate, mercapto-ester, epoxy glue, UV glue, and polydimethylsiloxane. In some other embodiments, the substrate 102 can be formed of a semiconductor (e.g., silicon, sapphire, and diamond). In some embodiments, the substrate 102 can be formed of glass. In some embodiments, the substrate 102 can have a thickness in a range of about 10 nm to about 0.5 cm.

One exemplary method for forming the substrate 100 using photolithographic techniques is discussed below in the Example section. Briefly, a plurality of metalized cavities having inverse pyramidal shapes can be formed in a semiconductor substrate. And the substrate can be used as a template to form a polymeric substrate having a plurality of metalized pyramidal projections distributed across a surface thereof.

The methods according to the present teachings can be employed to deliver a variety of cargos, including organic, inorganic and/or biological agents to a cell. In many cases, the cell's membrane is normally impermeable to such cargos. Some examples of such cargos include, without limitation, a deoxyribonucleic acid (DNA), a ribonucleic acid (RNA), an mRNA, a plasmid, a ribonucleic protein complex (RNP), a peptide, a protein, a dye, a drug, a therapeutic agent, among others. By way of example, the present substrates and methods can be employed to deliver a Cas9/gRNA RNP system to a cell. In some embodiments, molecules having a molecular weight in a range of about 500 Da to about 2,000,000 Da, e.g., in a range of about 10,000 Da to about 1,000,000 Da, can be delivered to cells using the methods and substrates according to the present teachings.

The present teachings can be used to deliver cargos to a plurality of different types of cells. Some examples of suitable cells include, without limitation, an epithelial cell, a neuron, a fibroblast, a stem cell (e.g., a skin stem cell), an hematopoietic cell, an immune cell (e.g., a T cell), a blood cell, bacteria, a plant cell, a liver cell, and a pancreatic cell. In some cases, the cells are Mammalian cells.

Figure 5:
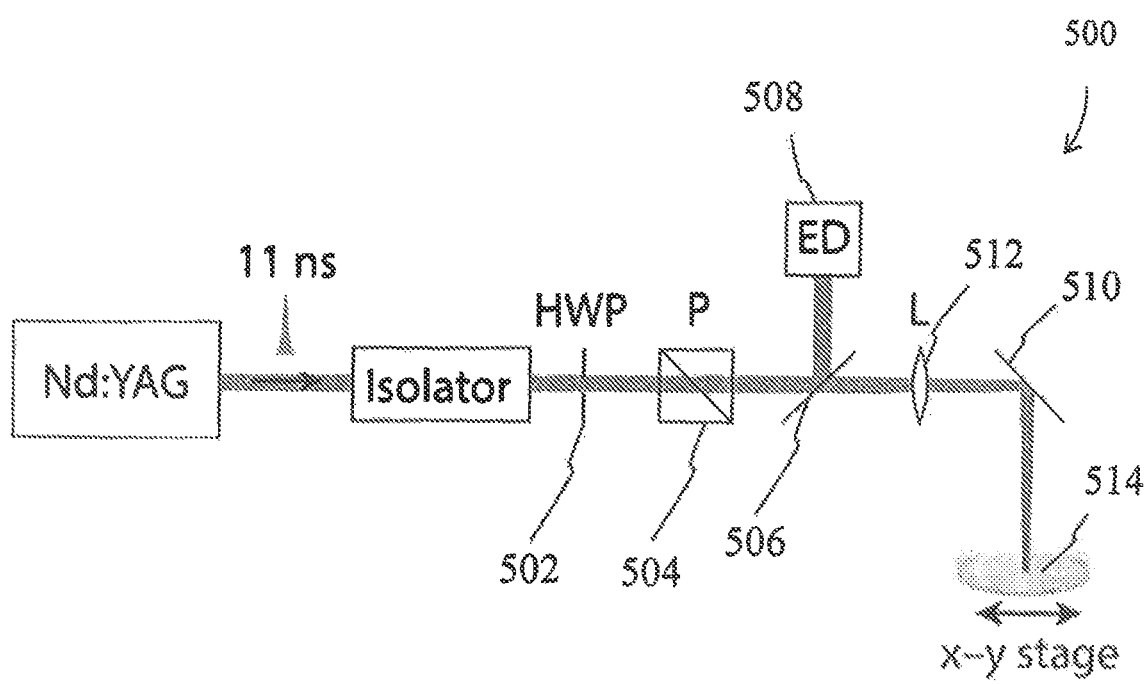
FIG. 5 is a schematic diagram of an exemplary apparatus for delivering cargos to cells in accordance with an embodiment of the present disclosure.

FIG. 5 schematically depicts a system for illuminating cells disposed on a thermoplasmonic substrate according to the present teachings so as to deliver one or more cargos to the cells. The system 500 includes a laser source 501 (e.g., a Nd:Yag laser in this embodiment) that generates a plurality of laser pulses. A variety of laser pulse widths can be employed. For example, the laser pulsewidths can be in a range of about 1 ns to about 1000 ns, e.g., in a range of about 10 ns to about 20 ns. In this embodiment, the laser pulses have a pulse width of about 11 ns. Further, in this embodiment, the laser pulses have a central wavelength of 1064 nm and a repetition rate of 50 Hz. The laser pulses pass through an isolator to prevent their back reflection and subsequently pass through a half-wave plate (HWP) 502 to rotate the plane of polarization of the laser pulses. The laser pulses then pass through a polarizer 504. By rotating the polarizer, the intensity of the pulses can be adjusted. A pelican beam splitter 506 directs a small portion of the energy of the pulses onto an energy detector 508 for measuring the pulse energies, and allows transmission of the remainder of the laser energy to a lens 512, which loosely focuses the pulses onto a substrate 514, via reflection at the mirror 510. The substrate can be seeded with a plurality of cells, typically disposed in a medium that contains one or more agents to be internalized by the cells. The substrate can be positioned on a movable X-Y stage that can be moved in two dimensions, e.g., at an average speed of about 10 mm/second, so as to expose different portions of the substrate on which the cells are disposed to the laser pulses.

In some embodiments, the central wavelength of the laser pulses can range from about 10 nm to about 2000 nm. Furthermore, in some cases, the fluence of the laser pulses at the substrate can be in a range of about 0.01 mJ/cm$^2$ to about 1000 mJ/cm$^2$, e.g., in a range of about 40 mJ/cm$^2$ to about 90 mJ/cm$^2$, or in a range of about 50 mJ/cm$^2$ to about 80 mJ/cm$^2$.

Figures 6A, 6B, 6C:
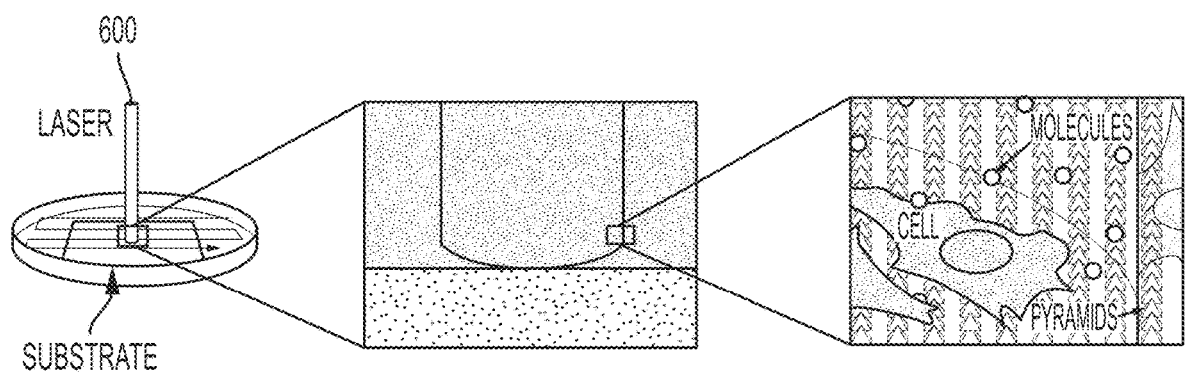
FIG. 6A is a schematic representation of an experimental set-up for irradiating a substrate to deliver cargos to cells in accordance with aspects of the present disclosure.
FIG. 6B is an enlarged view of a portion of the experimental set-up depicted in FIG. 6A.
FIG. 6C is an enlarged an irradiated portion of a cell-processing substrate irradiated by a laser beam as shown in FIG. 6B.

By way of further illustration, FIGS. 6A, 6B, and 6C schematically depict that the laser beam 600 can concurrently illuminate a plurality of pyramids on or in proximity of which cells are disposed. By way of example, the number of concurrently illuminated pyramids can be up to 500 million pyramids, e.g., in a range of about 100 million to about 500 million pyramids. The illumination of the pyramids by the continuous wave or pulsed laser radiation can in turn facilitate the uptake of one or more agents (e.g., molecules) on or in proximity of the pyramids (e.g., at a distance less than hundreds of nanometers (such as 1000 nm) relative to one or more pyramids). In this manner, the method of the present teachings allow parallel processing of a plurality of cells, thus providing an efficient method for delivering cargos to cells.

In some embodiments, the methods of the present teachings can be used to deliver cargos to cells at an efficiency of at least about 40%, e.g., in a range of about 60% to about 90%, and a cell viability of at least about 60%, e.g., in a range of about 60% to about 95%.

In some embodiments, the electrical conductive layer 300 has a substantially uniform thickness across the substrate surface. Further, the pyramidal projections can have substantially uniform heights and base lengths. Such uniformity can advantageously allow a consistent processing of cells disposed on different portions of the substrate surface.

In some embodiments, the methods according to the present teachings allow processing cells at a high throughput, e.g., at a throughput in a range of about 1 cell per min to about 500 million cells per minute, e.g., in a range of about 10 million cells per minute to about 500 million cells per minute, or in a range of about 50 million cells per minute to about 500 million cells per minute, or in a range of about 100 million cells per minute to about 500 million cells per minute. Further, the methods discussed herein allow the introduction of cargos into a variety of cells at a high efficiency (e.g., an efficiency greater than about 80%, or greater than about 90%) and with a high cell viability (e.g., a cell viability greater than about 80%, or greater than about 90%). Further, unlike some conventional methods, the use of the methods discussed herein for processing cells does not result in the introduction of cytoxic substances from the substrate (e.g., pieces of the conductive coating) into the processed cells.

In some aspects, the present invention provides a cartridge comprising a plasmonic substrate according to the present teachings and a device that can receive such a cartridge and illuminate cells disposed on the plasmonic substrate.

By way of example, FIG. 24 schematically depicts a cartridge 2400 comprising a housing 2401 in which a cell-processing substrate 2402 according to the present teachings, such as those discussed above, is disposed. As discussed above, the cell-processing substrate 2402 can include a surface 2402a (herein also referred to as a metalized surface) having a plurality of projections that are at least partially coated with an electrically conductive layer. In this embodiment, the cell-processing substrate 2402 is disposed between two polymeric layers 2404 and 2406. A gap 2408 between the metalized surface of the plasmonic substrate, i.e., the surface including the metal-coated pyramids, and the polymer layer 2406 allows injecting a sample containing cells onto the metalized surface of the plasmonic substrate 2402a via a port 2407 provided in the cartridge housing. The cartridge housing and the polymeric layers 2404 and 2406 can be formed of a variety of different polymers. By way of example, the cartridge housing can be formed of a polymer, such as polydimethylsiloxane (PDMS). Some suitable polymers for fabricating the polymeric layers 2404 and 2406 include, without limitation, PMMA and PDMS.

FIGS. 25A and 25B schematically depict a device 2500 that can receive the cartridge 2400 and illuminate a sample disposed on its metalized surface. The device 2500 includes a housing 2502 in which various components of the device are disposed. More specifically, the device 2500 includes a laser head 2504 that contains a laser source, e.g., a diode laser, and the associated electronics for generating a laser beam for the illumination of a sample disposed on the metalized surface of a plasmonic substrate, as discussed in more detail below. Some examples of laser include, without limitation, continuous-wave lasers and pulsed lasers, e.g., lasers generating nanosecond or femtosecond radiation.

The housing 2502 further includes an enclosure 2506 having a slot 2506a through which the cartridge 2400 can be inserted into the enclosure to be placed in the path of the laser beam generated by the laser head 2504. In this embodiment, an x-y scanning module 2508 can scan the laser beam over the metalized surface of the plasmonic substrate of the cartridge so as to illuminate different portions thereof, e.g., the portions in contact with the sample containing cells. The x-y scanning module can be implemented in a variety of different ways. By way of example, the scanning module can include two rotatable mirrors that rotate about orthogonal axes.

More specifically, in this embodiment, a beam splitter 2507 reflects a small portion of the laser beam to an energy meter 2509 while allowing the rest of the laser beam to pass therethrough to reach the x-y scanning module 2508, which scans the beam over a sample disposed on the metalized surface of the cartridge.

In this embodiment, the polymeric layer 2406 is selected to be substantially transparent to the laser radiation, thereby allowing efficient illumination of a sample disposed on the metalized surface of the cell-processing substrate via the laser radiation.

The device 2500 further includes a hardware module 2510 that can include control circuitry and associated electronics for operating and controlling the device, e.g., for controlling the scanning module and the laser.

With reference to FIG. 26, in use, a user can introduce, e.g., via a syringe, a sample, e.g., a sample containing cells, onto the metalized surface of the cell-processing substrate contained in the plasmonic cartridge. The cartridge can then be inserted into the device 2500 to be exposed to laser radiation. The scanning module can scan the laser radiation over different locations of the metalized surface of the plasmonic substrate so as to expose portions of the sample disposed at those locations to the radiation.

Example 1

Fabrication of Thermoplasmonic Substrates

Figure 7A:
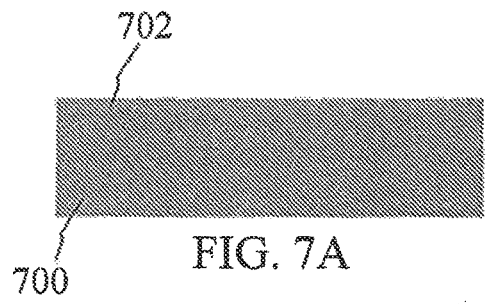
FIGS. 7A-7J schematically depict various steps in a method for fabricating a thermoplasmonic substrate according to an embodiment of the present teachings.
Figure 7B:
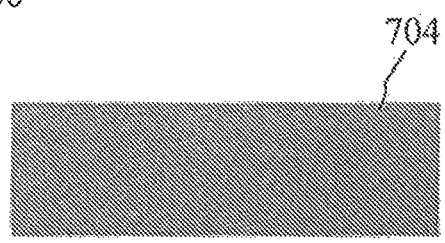
Figure 7C:
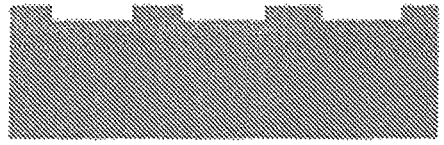
Figure 7D:
Figure 7E:
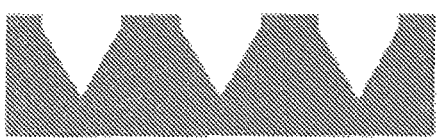
Figure 7F:
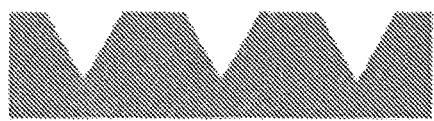

Thermoplasmonic substrates were fabricated using silicon master templates. Specifically, silicon master templates were fabricated using the following methods. A silicon wafer 700 was sonicated in acetone (5 min) and methanol (5 min) before being rinsed in isopropyl alcohol (IPA) (FIG. 7A). $O_2$ plasma cleaning of the wafers was then performed (100 W, 20 mT, 1 min). A chromium (Cr) hard lithographic mask 702 was then deposited on the wafer via thermal evaporation (Cr thickness=150 Å). The wafer was baked (200° C., 3 min) to evaporate all solvents before processing. An SPR 700-1 photoresist 704 was spin-coated onto the wafer (3000 RPM, 45 s, ramp of 1000 RPM/s). The wafer was then soft baked (115° C., 60 s) (FIG. 7B). The entire area of the silicon wafer was exposed in an autostepper to form a grid-based pattern. A post-exposure bake was performed (115° C., 60 s). The wafer was then developed in CD-26 developer (1 min), then rinsed with deionized (DI) water (20 s). Development was repeated until no residue was released into the developer. The plasma stripper was then used to descum the wafer (100 W, 20 mT, 15 s) (FIG. 7C). A chromium etch was performed (12 s, 15 angstroms/s etched, room temperature) to remove the Cr in the exposed squares. The sample was then washed with DI water and dried with an $N_2$ gun. The photoresist was removed in acetone. An $O_2$ plasma clean was performed (100 W, 20 mT, 3 min) to completely remove residual photoresist (FIG. 7D). An HF etch (4.9% HF) was used to remove oxide formed on the silicon (15 s). A KOH etch (2 parts water and 1 part of 45% KOH), was performed on a hotplate with a thermometer to form a plurality of inverted pyramids in the substrate (80° C., 3 min) (FIG. 7E). Chromium etching was performed to remove the hard mask (20 s, room temperature) (FIG. 7F).

Figure 7G:
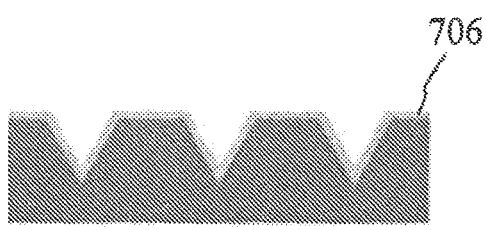
Figure 7H:
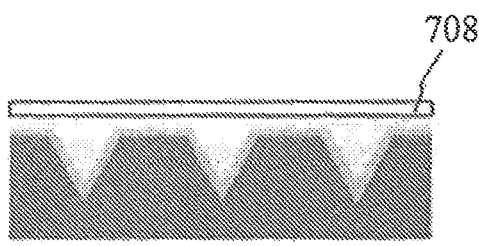
Figure 7I:
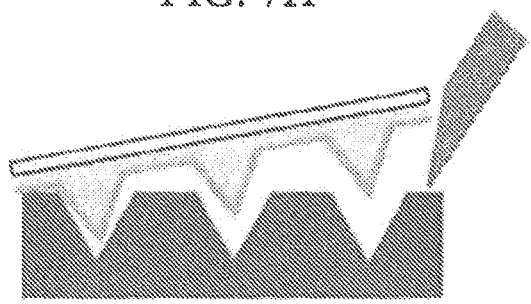
Figure 7J:
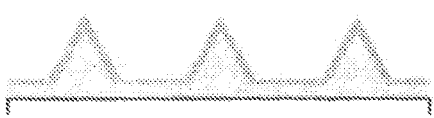

The thermoplasmonic substrates were formed in the following way. A gold layer 706 was deposited via an electron beam evaporator on a silicon master template (gold thickness=50 nm) (FIG. 7G). A glass coverslip 708 (no. 1.5) was glued to the gold-coated master template with UV curable glue (Norland Adhesive 61) and cured under the UV lamp overnight (FIG. 7H). A thermoplasmonic substrate was peeled off ("template-strip") from the template using a razor blade (FIG. 7I) resulting in a final substrate with about 10 million pyramids (FIG. 7J). By repeating gold deposition and template-stripping, large quantities of thermoplasmonic substrates were fabricated with high precision. The master template for the fabrication of the thermoplasmonic substrate can be re-used hundreds of times for template-stripping. This approach allows for low-cost, highly-precise, and highly-reproducible fabrication of thermoplasmonic substrates.

Figure 8A:
FIG. 8A is an image of a thermoplasmonic substrate in accordance with an embodiment of the present disclosure.

FIG. 8A shows an image of a thermoplasmonic substrate that is comparable in size to a U.S. quarter.

Figure 8B:
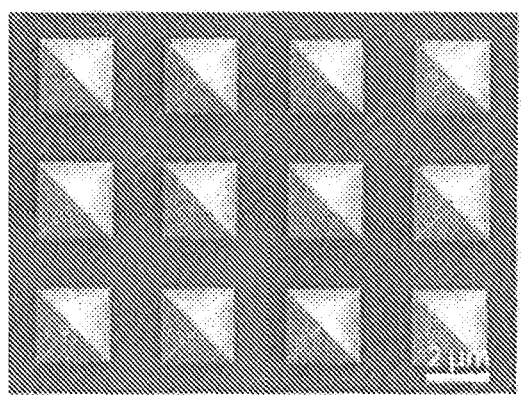
FIGS. 8B and 8C are, respectively, a scanning electron microscopy image of a top view and a side view of a thermoplasmonic substrate in accordance with an embodiment of the present disclosure.
Figure 8C:
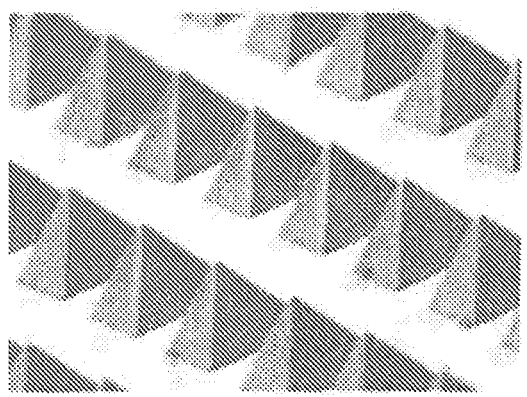

FIGS. 8B and 8C show, respectively, a scanning electron microscopy (SEM) image of a top view, and an SEM image of a side view, of thermoplasmonic substrates formed using the above process. Characterization through SEM confirms that the pyramids of the template-stripped thermoplasmonic substrates are highly uniform in base lengths (2.4 µm), spacings (1.4 µm), and heights (1.4 µm), and consistent from batch to batch.

Example 2

Temperature Simulation of Thermoplasmonic Substrates

Figure 9A:
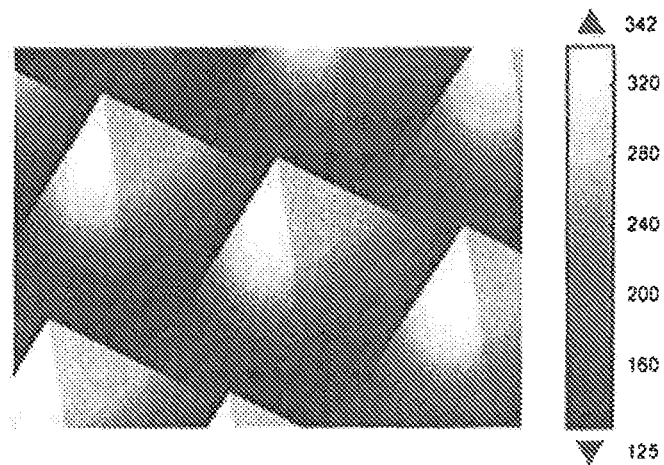
FIGS. 9A and 9B show the results of Fine Element Method simulations of temperature profiles of a plurality of pyramids of a thermoplasmonic substrate according to an embodiment of the present teachings when illuminated with laser radiation.
Figure 9B:
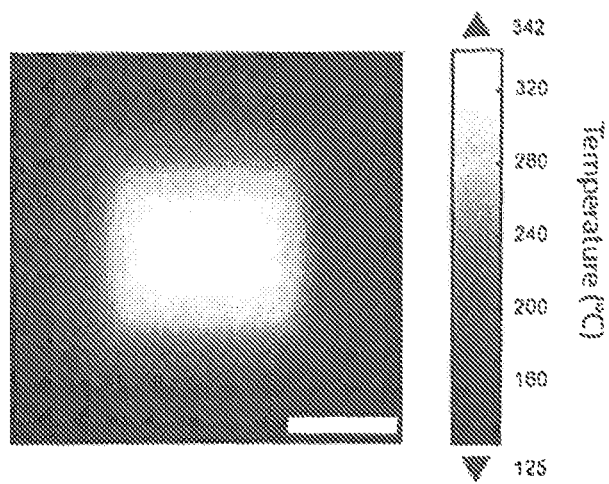
Figure 9C:
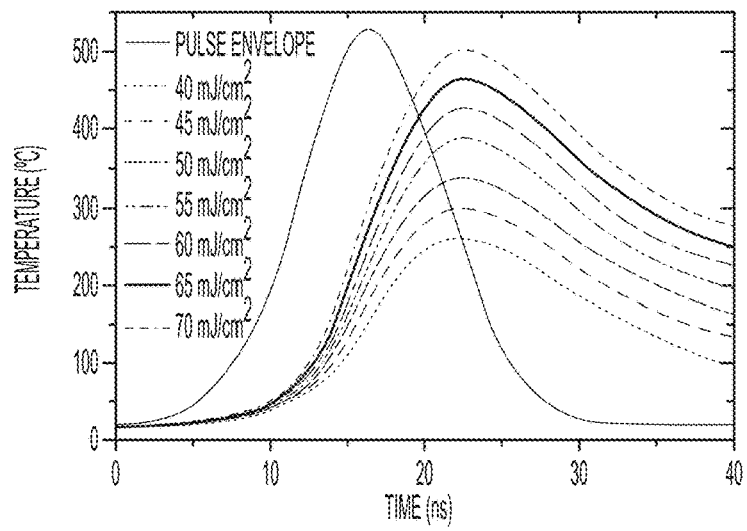
FIG. 9C presents a plurality of graphs depicting simulated temporal evolution of the maximum water temperature near nano-hotspots of a thermoplasmonic substrate in accordance with an embodiment of the present teachings for different laser fluences.
Figure 9D:
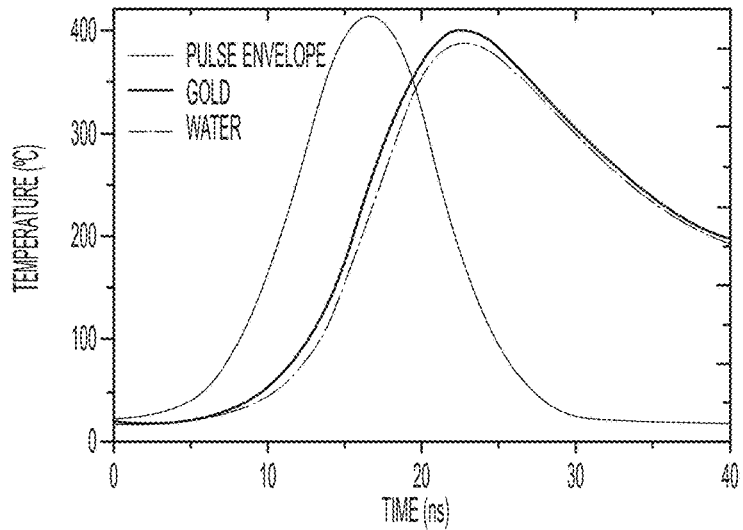
FIG. 9D presents a plurality of graphs depicting simulated temporal evolution of the maximum temperature of water and gold associated with a thermoplasmonic substrate according to an embodiment of the present teachings for a laser fluence of 55 $mJ/cm^2$.
Figure 9E:
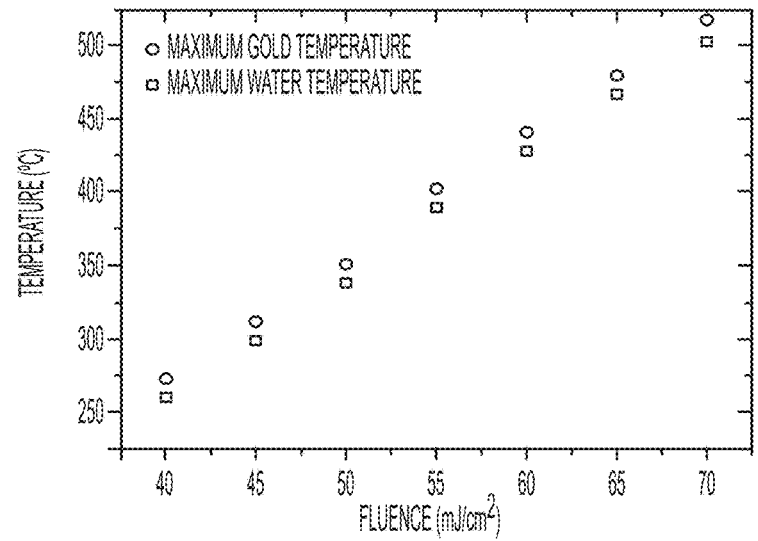
FIG. 9E is a plurality of data points depicting simulated maximum temperature of water disposed on a thermoplasmonic substrate according to an embodiment of the present teachings and gold associated with the substrate for different laser fluences.

Numerical simulations were performed to image the temperature profile of laser-irradiated pyramids (FIGS. 9A-B) of thermoplasmonic substrates and to determine the threshold laser fluence required for the temperature at the pyramidal apex of a thermoplasmonic substrate to reach the temperature range necessary to form bubbles within an aqueous environment (FIGS. 9C-E).

Without being limited to any particular theory, the pyramids of the thermoplasmonic substrates are effective nano-heaters due to the combined effect of their thin metal film, sharp apex, and gold composition, making them ideal for thermoplasmonic applications. Sharp metallic nanostructures are ideal for absorbing laser energy and concentrating the energy to hotspots that heat an aqueous environment and generate bubbles.

The light-substrate interactions in an aqueous environment was simulated using a Finite Element Method (Comsol, Multiphyiscs 4.4). First, the three-dimensional electromagnetic interaction was calculated using the scattered field formulation under the assumptions that the spot size was large compared to the periodic pyramid structure (plane wave approximation) and that the optical properties of the polymer, gold film and adjacent water did not change during the interaction with the linearly polarized 11 ns (FWHM) Gaussian pulses. The geometrical parameters (pyramid base length: 2.4 µm; spacing: 1.2 µm; and thickness of the gold layer: 50 nm) were chosen to resemble those of the fabricated samples. Periodic boundary conditions in the x and y directions were applied. The simulation domain in the z-direction was truncated using perfectly matched layers (PML). The calculated laser energy absorbed was used as a transient heat source for a one-temperature model. The spatial and temporal evolution of the gold and water temperature was calculated for different laser fluences. More details about the setup of the simulation can be found in Demesy et al., "Tridimensional Multiphysics Model for the Study of Photo-induced Thermal Effects in Arbitrary Nanostructures", JEOS:RP, 2011, vol. 6, 11037. The physical properties of gold and water were taken from Ekici et al., "Thermal Analysis of Gold Nanorods Heated with Femtosecond Laser Pulses" J. Phys. D Appl. Phys., 2008, 41(18), 185501. Properties of the UV glue were provided by the manufacturer.

FIG. 9A shows a perspective view generated by Finite Element Method simulation of a thermoplasmonic substrate according to the present teachings, demonstrating that the thermoplasmonic pyramidal apexes reach a maximum temperature of 342° C. at a laser fluence of 45 mJ/cm$^2$. FIG. 9B shows a top view generated by Finite Element Method simulation of a pyramid from the thermoplasmonic substrate depicting the temperature distribution of the pyramid. FIG. 9C shows a plurality of graphs depicting the temporal evolution of the maximum water temperature near nano-hotspots of a thermoplasmonic substrate for different laser fluences, and FIG. 9D shows a plurality of graphs depicting the temporal evolution of the maximum temperature of water and gold for a laser fluence of 55 mJ/cm$^2$. The envelope of the excitation pulse is indicated in gray in both FIGS. 9C and 9D. FIG. 9E shows a the maximum water and gold temperature for different laser fluences.

The simulation results show that for fluences above 40 mJ/cm$^2$, the aqueous environment within tens of nanometers surrounding the pyramidal apex reaches temperatures above 300° C., which are within the temperature range for bubble formation. The critical temperature of water at 1 atm is in a range of 367° C. to 377° C., and thermodynamic theory and experimental studies show that explosive boiling occurs where temperatures reach 80-90% of this critical value, which corresponds to temperatures between 293-340° C.

The laser experiments with cells were performed above the threshold laser fluence necessary for bubble formation (40 mJ/cm$^2$).

Example 3

Laser Scanning of Thermoplasmonic Substrates

Figure 10:
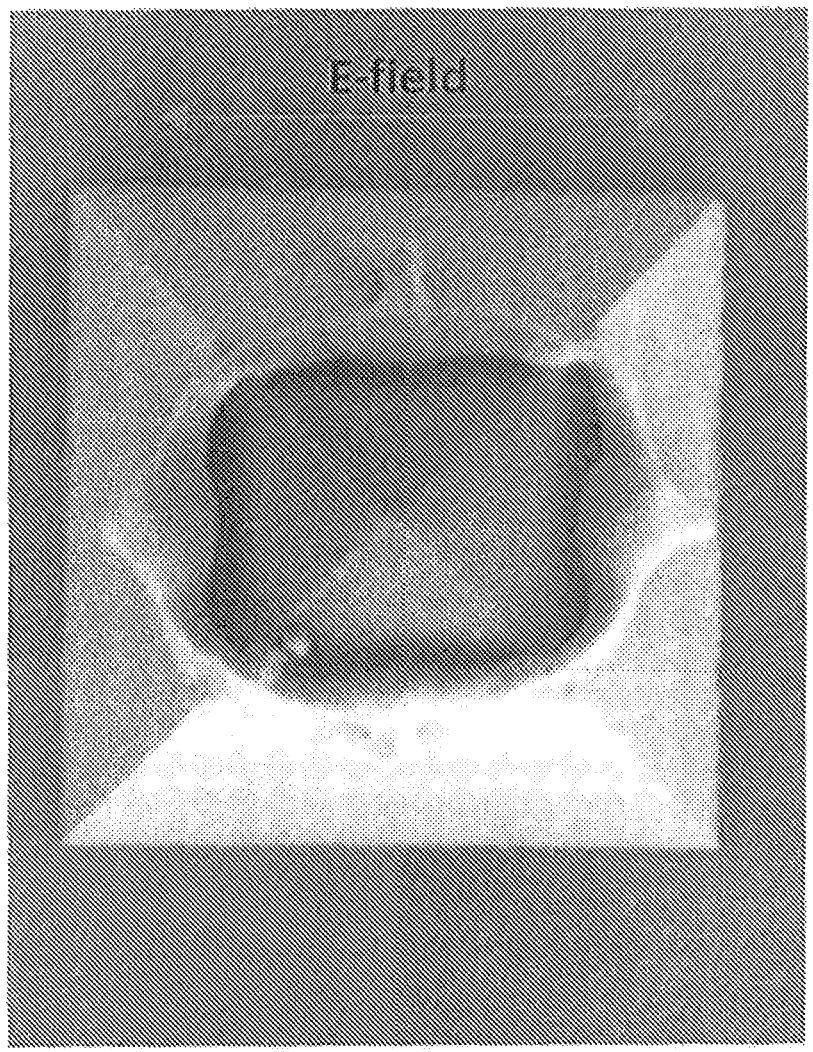
FIG. 10 is a scanning electron microscopy image of a top view of a thermoplasmonic substrate according to an embodiment of the present teachings after laser illumination at a fluence of 200 $mJ/cm^2$.

Thermoplasmonic substrates were illuminated at a high fluence and characterized through scanning electron microscopy (SEM) to determine the damage done to the pyramids after laser illumination. FIG. 10 shows an SEM image of a top view of a thermoplasmonic substrate after laser illumination at a fluence of 200 mJ/cm$^2$ demonstrating the melting of the thin gold film above the pyramid and no visible effect on the polymer layer under the gold film.

The laser experiments with cells were performed below the point where the gold film at the pyramidal apex is damaged (200 mJ/cm$^2$).

Example 4

Seeding Cells on Thermoplasmonic Substrates

HeLa cells were seeded on thermoplasmonic substrates. HeLa CCL-2 cells were cultured in DMEM (10% FBS, 1% penicillin streptomycin) and incubated (37° C., 5% $CO_2$). Cells were passaged every other day, and used for experiments at 80% confluence, between passage numbers 15-30. Cells were washed with PBS (8 mL) and incubated (3 min) with trypsin (5 mL), before being neutralized with cell media (13 mL). Pipetting was used to wash the bottom of flask 5 times with the cell mixture before transferring the cell mixture to a tube (15 mL) and centrifuging it (5 min, 125 g). The supernatant was removed gently with vacuum pipette and cells were re-suspended in fresh media (8 mL) and pipetted 30 times (up and down counted as 1 time). Countessa cell counter was used to measure cell density and viability. Healthy cells have 90-99% viability. 8 template-stripped substrates were taped lightly to the bottom of a petri dish (100 mm) with double-sided Kaptone tape. 5 million cells were suspended in fresh cell media (15 mL) and added to the petri dish for overnight incubation.

Example 5

Chemically Fixing Cells on Thermoplasmonic Substrates

HeLa cells were chemically fixed on thermoplasmonic substrate. Samples were soaked in fixing solution (1 part 25% glutaraldehyde, 1 part 1M Hepes, 8 parts millipore water) (≤10 min). Samples were soaked in buffer solution (2 parts 1M Hepes, 8 parts millipore water) and wrapped with parafilm before overnight storage (5° C.). The following day, the samples were rinsed by soaking in millipore water (≤5 min). The samples were then dehydrated with ethanol by soaking them in 50% ethanol (5 min), 70% ethanol (5 min), 90% ethanol (5 min), 100% ethanol 3 times (≤7 min each, total of 20-30 minutes), and 100% ethanol with molecular sieves (grade: 3 Angstrom) (7 min). Samples were finally soaked in HMDS 3 times (≤7 min each, total 20-30 minutes) before air drying at room temperature.

The morphology of HeLa cells on thermoplasmonic substrate was imaged using scanning electron microscopy (SEM) and confocal microscopy techniques.

Figure 11A:
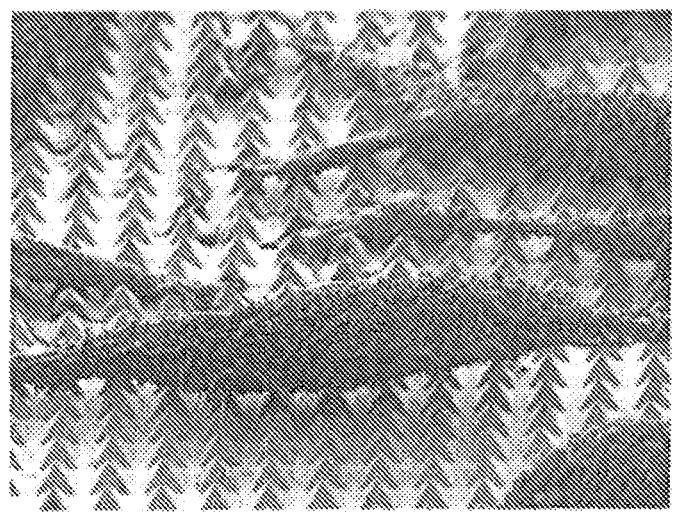
FIG. 11A is a scanning electron microscopy image of a chemically-fixed cell disposed on pyramids of a thermoplasmonic substrate according to an embodiment of the present teachings.
Figure 11B:
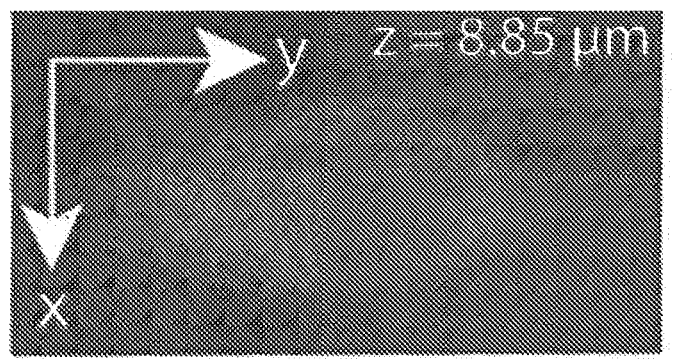
FIG. 11B is a confocal laser-scanning microscopy image of a slice of a cell (40 μm in length) with calcein red-orange AM fluorescence at z=8.85 μm as measured from the bottom of the cell.
Figure 11C:
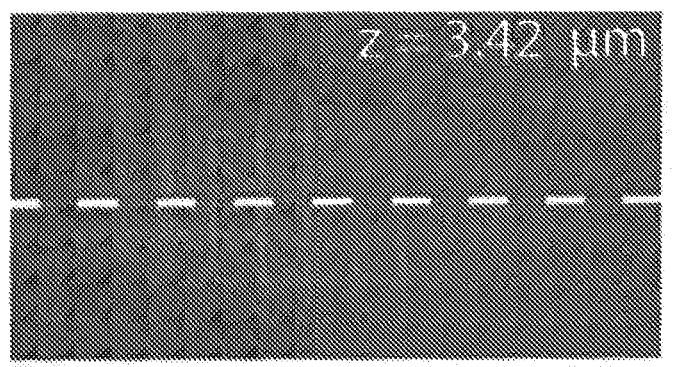
FIG. 11C is a confocal laser-scanning microscopy image of a cell closer to the bottom of the cell.
Figure 11D:
FIG. 11D depicts z-stack cross section of the cell along the dotted white line shown in FIG. 11C.

FIG. 11A shows an SEM image of a chemically-fixed cell on pyramids of a thermoplasmonic substrate. Because chemical fixation kills the cell and alters the cell's lipid membranes, confocal microscopy was additionally used to image the morphology of a living cell that was fluorescently tagged with a cell-permeant dye for living cells (FIGS. 11B-D). FIG. 11B shows a confocal laser-scanning microscopy image of a slice of a cell (40 μm in length) with calcein red-orange AM fluorescence at z=8.85 μm as measured from the bottom of the cell. The confocal slice reveals regular cell morphology. FIG. 11C shows a scan closer to the bottom of the cell at z=3.42 μm that makes pyramids appear in a dark grid-like pattern as the pyramids do not fluoresce in this channel. A z-stack cross section of the cell along the dotted white line from FIG. 11C is shown in FIG. 11D and depicts the membrane adhering to the pyramids. Both imaging methods indicate that each cell adheres to approximately 40-50 pyramids.

Example 6

Intracellular Delivery of Cargo

The thermoplasmonic substrates were laser scanned to perform intracellular delivery of cargo. Substrates with Hela cells on the surface were transferred to a petri dish (35 mm) and pre-warmed with PBS solution (2 mL, 37° C.) containing the molecules to be introduced into the cells (Calcein green at 500 μM or FITC-Dextran at 25 mg/mL). The laser setup (FIG. 5) included an Nd:YAG source generating laser pulses at a wavelength of 1064 nm. The pulses were 11 ns in duration, with a repetition rate of 50 Hz. The laser passed through an optical isolator and a half-wave plate (HWP) and polarizer (P) that was controlling the laser energy passing through the setup. The half-wave plate was software-controlled, so the laser energy was changed remotely. A pelican beam splitter sent 8% of the beam to an energy detector (ED) to constantly monitor the energy during an experiment. A lens (L) loosely focused the beam (1.2 mm in diameter) on the sample which sat on an x-y translational stage.

For the fluence experiments (FIG. 12A-12H), the laser was scanned in a line across the sample, with each line at a different fluence. Longer distances were scanned to avoid cells being affected by the acceleration and deceleration of the stage (scan speed of 10 mm/s and Δx of 100 mm), which can change the number of pulses hitting the sample and can affect the viability and efficiency of the technique. For flow cytometry experiments (FIGS. 16-19) the exact same procedure as the fluence scanning experiments were used and the entire sample was scanned (scan speed: 10 mm/s, Δx: 100 mm, Δy: 0.5 mm, total time ~10 min). The petri dish contained the dye to be delivered in PBS solution. Negative control of areas with pyramids and no laser irradiation, and areas with no pyramids and no irradiation were performed on the same sample for each experiment.

The intracellular delivery of cargo at high efficiency and viability with no damage to the substrate was demonstrated using SEM and fluorescence microscopy techniques.

Figure 12A:
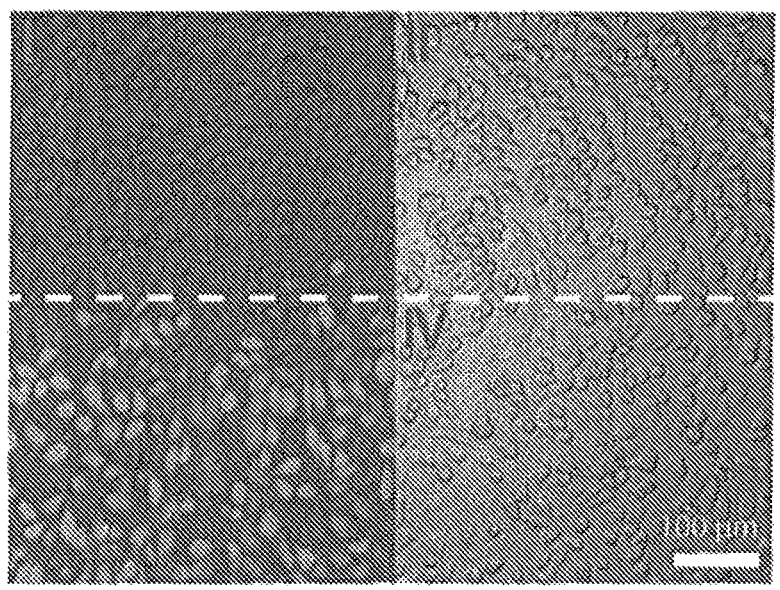
FIG. 12A is an overlay of a bright-field and fluorescent images of cells disposed on different portions of a surface of a thermoplasmonic substrate according to an embodiment of the present teachings, where areas I and III have pyramids, areas II and IV are flat gold. The laser radiation was scanned below the dotted line, and area III was the only region in which green molecules were delivered to cells.

Hela Cells were cultured on a thermoplasmonic substrate fabricated as discussed above, put in a solution containing dissolved cargo, laser-scanned, and imaged using fluorescence and dark-field microscopy techniques. FIG. 12A shows a bright-field image overlaid with a fluorescent image with excitation and emission wavelengths of 495/515 nm, respectively of the cells after laser illumination with dissolved Calcein green molecules. Areas I and III contain gold-coated pyramids, whereas areas II and IV are flat gold. Areas III and IV were laser-scanned, while areas I and II were not. Only area III—the area containing gold-coated pyramids that was irradiated by the laser radiation—demonstrates the successful delivery of cell-impermeable Calcein green molecules to the cells. This observation confirms that gold-coated pyramids in combination with laser-irradiation leads to the delivery of molecules into cells. Furthermore, the pyramidal surface on the left reflects less light than the flat gold on the right, making the surface appear darker. This demonstrates that the technique offers spatially-selective delivery, and works only when cells are cultured on pyramids and laser-scanned.

Automated cell counting was performed on fluorescent images to determine how many cells had cargo delivered to the cytoplasm (efficiency), and how many of those cells were alive after irradiation (viability). Cell counting was done with a Fiji Image processing software using fluorescent images of the samples. The final cell count was checked to make sure that none of the cells was missed, and additional cells were added in the cell counter window. The following definitions were used to calculate viability and efficiency percentages: Viability=$N_{CAM\ Red}/N_{average}$ and Efficiency=$N_{green}/N_{average}$, where $N_{CAMRed}$ is the number of alive cells (in red) in the field of view, $N_{average}$ is the average number of alive cells in a not laser-treated area, and $N_{Green}$ is the number cells that appear green due to delivery of green macromolecules. Cell counting was always performed on a region of the same size across different samples. Triplicate experiments were performed for all data sets.

Figure 12B:
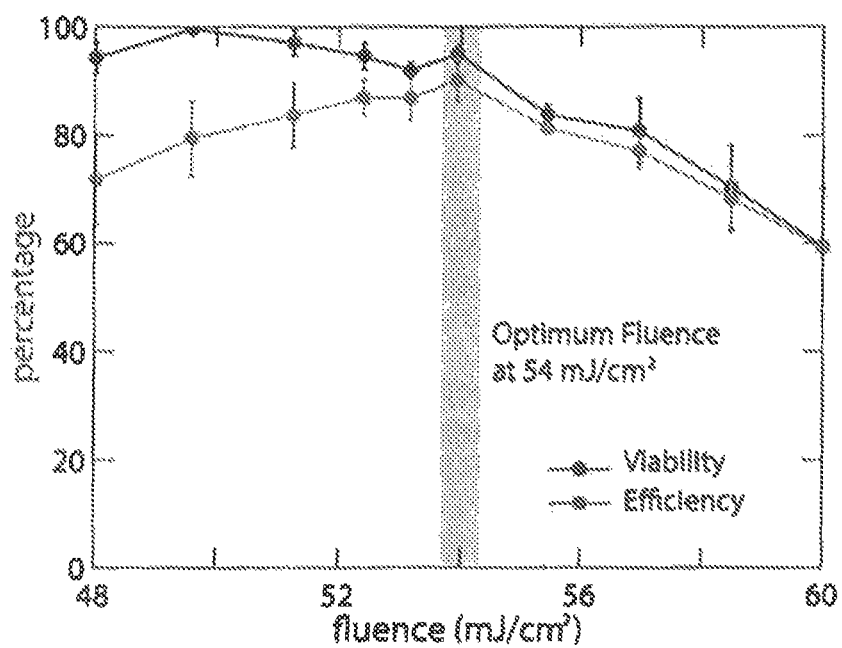
FIG. 12B is a plurality of graphs depicting the delivery efficiency and viability as a function of laser fluence (data represent mean±SE from n=3 independent experiments) for cells disposed on a thermoplasmonic substrate in accordance with an embodiment of the present disclosures.
Figure 12C:
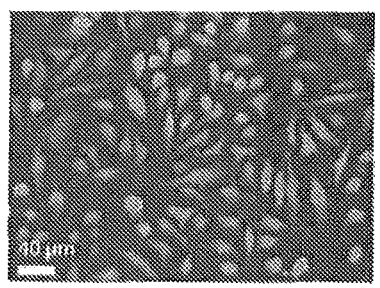
FIG. 12C is a fluorescent image of cells after calcein green delivery in accordance with aspects of the present disclosure.
Figure 12D:
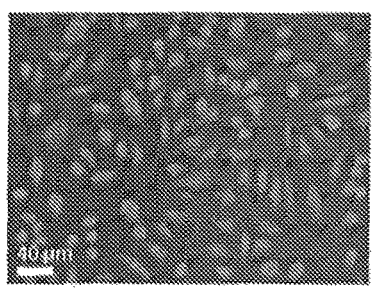
FIG. 12D is a fluorescent image of cells depicting cell viability after delivery of calcein red-orange AM.
Figure 12E:
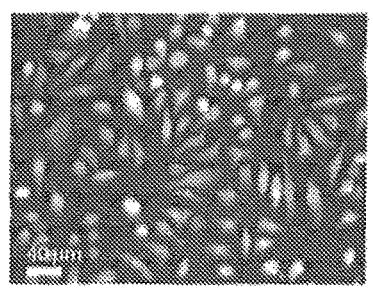
FIG. 12E is an image depicting an overlay of the images from FIG. 12C and FIG. 12D.

The efficiency of cargo delivery to HeLa cells that were cultured on the thermoplasmonic substrate and laser-scanned was determined using Calcein green molecule (FIG. 12C). A second dye, Calcein red-orange AM, was used to check the post-experimental viability of the cells (FIG. 12D). An overlay of the efficiency and viability shows that cells with Calcein green delivered to the cytoplasm survive the experiment (FIG. 12E).

The experiment was repeated at different laser fluences to determine the optimum laser fluence for maximum delivery efficiency and viability (FIG. 12B). Each laser fluence experiment was repeated on 3 separate substrates, in 3 separate dishes, for triplicate (n=3) results. The optimum fluence, where both efficiency (90%) and viability (95%) are maximized, was found to be 54 mJ/cm$^2$. Simulation results previously discussed showed that the local temperature reaches 370° C. at this fluence, which is in the temperature range for bubble formation.

Figure 12F:
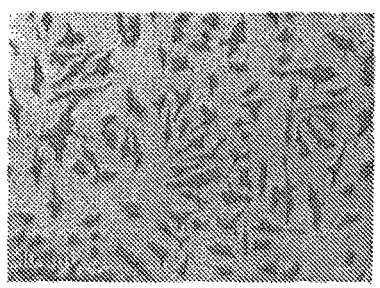
FIG. 12F is a scanning electron microscopy image of a top view of cells chemically fixed to a thermoplasmonic substrate according to an embodiment of the present disclosure.
Figure 12G:
FIG. 12G is an image depicting an overlay of the images from FIG. 12E and FIG. 12F.
Figure 12H:
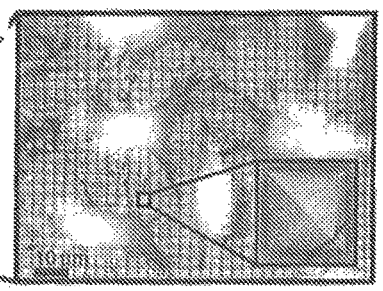
FIG. 12H is an enlarged view of the portions of the FIG. 12G depicted in the rectangle.
Figure 13A:
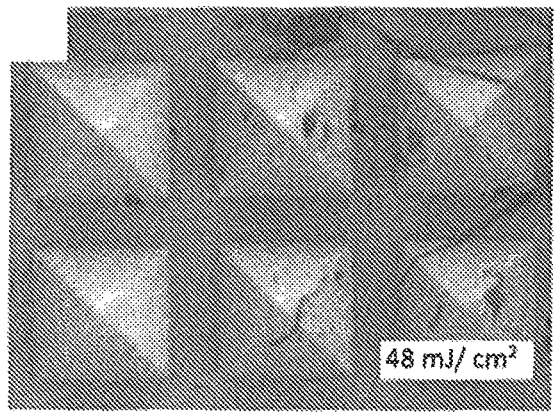
FIG. 13A is a scanning electron microscopy image of a top view of a thermoplasmonic substrate after delivering cargos to cells using a laser illumination at a fluence of 48 $mJ/cm^2$.
Figure 13B:
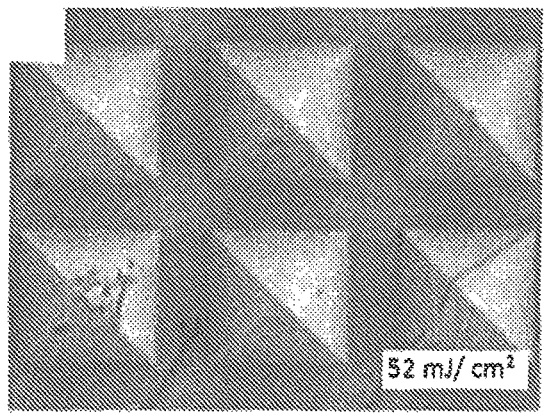
FIG. 13B is a scanning electron microscopy image of a top view of a thermoplasmonic substrate after delivering cargos to cells using a laser illumination at a fluence of 52 $mJ/cm^2$.
Figure 13C:
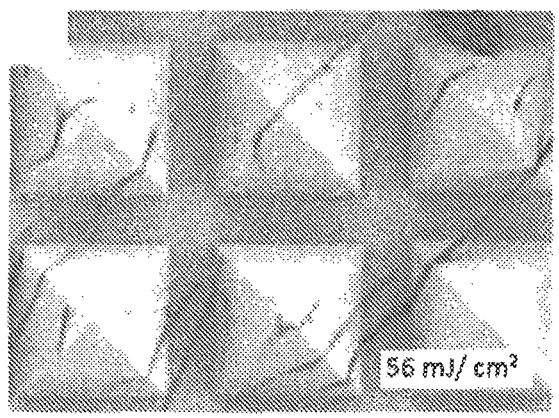
FIG. 13C is a Scanning Electron Microscopy image of a top view of a thermoplasmonic substrate after delivering cargos to cells using a laser illumination at a fluence of 56 $mJ/cm^2$.
Figure 13D:
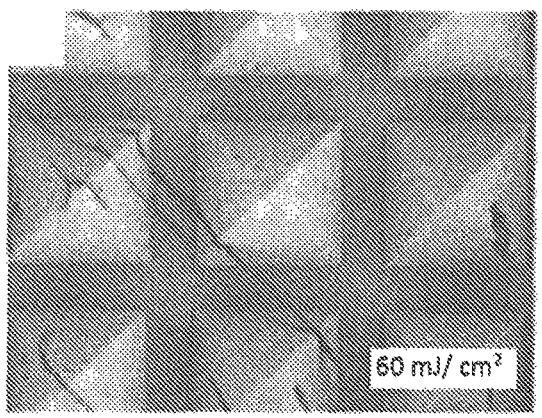
FIG. 13D is a Scanning Electron Microscopy image of a top view of a thermoplasmonic substrate after delivering cargos to cells using a laser illumination at a fluence of 60 mJ/cm$^2$.

The cells were chemically fixed after laser scanning and an SEM image of the substrate was taken in order to determine if the pyramids experience any damage or melting during laser exposure at the optimum fluence of 54 mJ/cm$^2$ (FIG. 12F). No visible damage was observed to individual pyramids in the laser-treated area despite having been exposed to a fluence of 54 mJ/cm$^2$ and despite having undergone intense thermoplasmonic heating at the apex (inset of FIG. 12H). Furthermore, no damage was observed on substrate after laser experiment at different fluence scans, such as at 48 mJ/cm$^2$ (FIG. 13A), 52 mJ/cm$^2$ (FIG. 13B), 56 mJ/cm$^2$ (FIG. 13C), and 60 mJ/cm$^2$ (FIG. 13D).

All consecutive experiments were performed at the optimum fluence of 54 mJ/cm$^2$ because it offers the highest efficiency and viability, and no visible damage.

Example 7

Cargo Distribution Within Cells

Figure 14A:
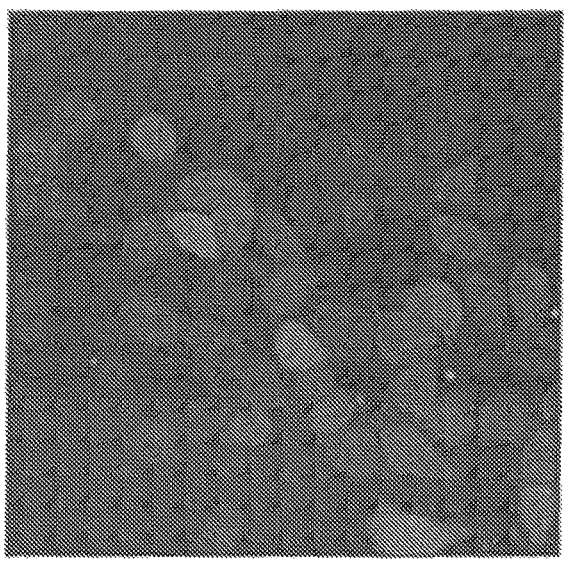
FIG. 14A is a fluorescent image of cells with 150 kDa FITC-Dextran in FITC channel (same scale bar as FIG. 14B)
Figure 14B:
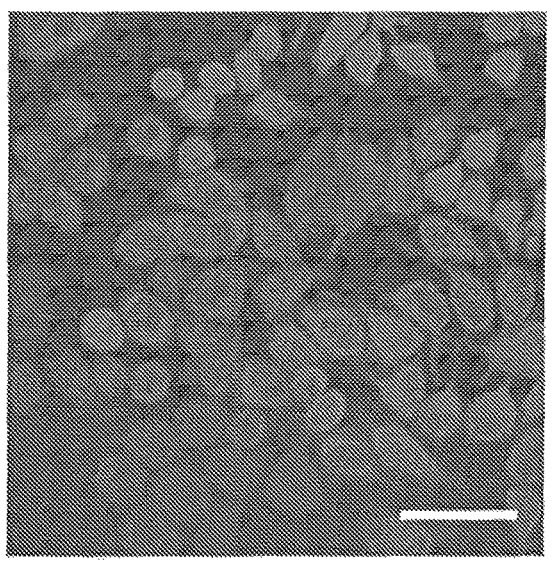
FIG. 14B is a fluorescent image of cells with 150 kDa FITC-Dextran in calcein AM channel(scale bar is 50 μm)

The distribution of cargo delivered to the cytoplasm of the cell was demonstrated using fluorescence microscopy. FITC-dextran 150 kDa was delivered into the cytoplasm of the cells and distributed evenly within each cell (FIG. 14A) while keeping most of the cells viable (FIG. 14B).

Example 8

Cells Proliferation After Cargo Delivery

Figure 15A:
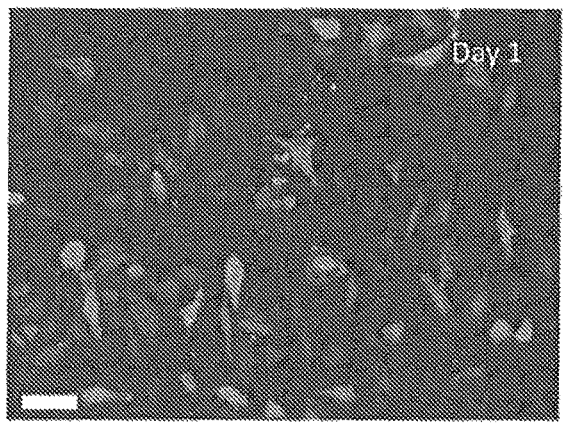
FIG. 15A is a fluorescent image of cells with 150 kDa FITC-Dextran 24 hours after delivery in FITC-Dextran channel (scale bar, 50 μm)
Figure 15B:
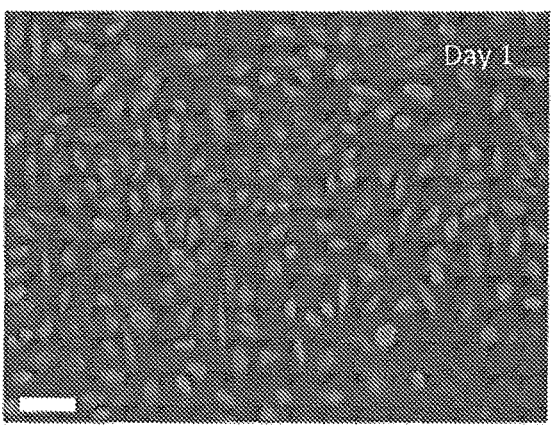
FIG. 15B is a fluorescent image of cells with 150 kDa FITC-Dextran 24 hours after delivery in calcein AM channel (scale bar, 50 μm)
Figure 15C:
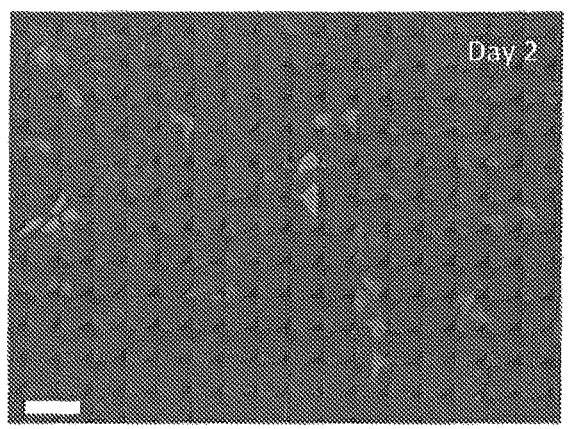
FIG. 15C is a fluorescent image of cells with 150 kDa FITC-Dextran 48 hours after delivery in FITC-Dextran channel (scale bar, 50 μm)
Figure 15D:
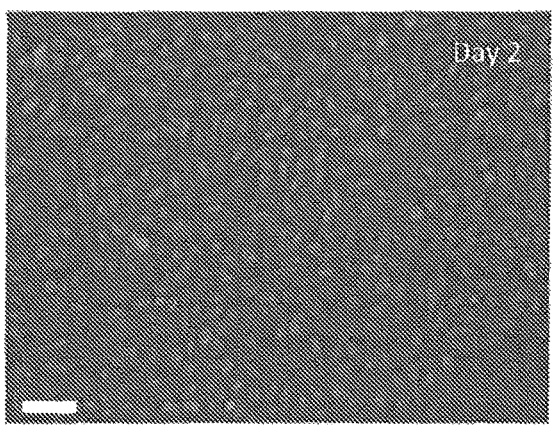
FIG. 15D is a fluorescent image of cells with FITC-Dextran 150 kDa 48 hours after delivery in calcein AM channel (scale bar, 50 μm)

The proliferation of the cells after thermoplasmonic treatment was demonstrated using fluorescence microscopy. The cells were imaged after 24 hours and 48 hours of FITC-dextran 150 kDa delivery (FIGS. 15A and 15C) and Calcein AM delivery (FIGS. 15B and 15D). The cells showed the retention of FITC-dextran 150 kDa after 48 hours of delivery. The cells also showed an increase in density after 48 hours, indicating that the cells not only remain viable but continue to divide after laser illumination.

Example 9

Residual Gold After Cargo Delivery

The gold content in the cells after laser experiments was measured using inductively coupled plasma mass spectroscopy (ICP-MS). Even though cells may appear viable after undergoing intracellular delivery with this technique, there is a potential risk of DNA mutations if gold nano-fragments remain in the cell.

Prior to performing ICP-MS analysis, the samples were first weighed out on an analytical balance into clean BD Falcon tubes (15 ml) and then digested using ultrapure hydrochloric acid overnight. The next day, samples were diluted to a desired volume (usually 5 or 10 ml) with deionized water. A fresh calibration curve was run with the sample. A method blank was run with the batch of samples (this was also used to calculate the detection limit) and calibration verification standards were run to calculate percent recoveries.

FIG. 16 shows a table summarizing the results from the ICP-MS analysis for dextran 10 kDa cargo. Cells that undergo thermoplasmonic intracellular delivery had a signal that is representative of background noise, as did cells that were not in contact with gold. ICP-MS measurements on cells that were incubated with gold nanoparticles (and then washed several times to remove floating nanoparticles) exhibited greater gold content than background noise. ICP-MS verifies that no gold residue remains in the cells post-experiment, therefore excluding risks of gold fragment-induced mutagenesis.

Example 10

Flow Cytometry Analysis of Cells

Cargos of different cargo sizes were delivered to Hela cells for flow cytometry measurements to quantify the efficiency and viability of the intracellular delivery technique. Flow cytometry measures the scattered forward and side light, and the fluorescence of cells passing through a beam of light. The forward scattering gives information about the size of a cell, while the side scattering provides information about the internal granularity. A range of cargos (Calcein green 0.623 kDa, Dextran 10 kDa, Dextran 70 kDa, Dextran 150 kDa, Dextran 500 kDa, Dextran 2000 kDa) was delivered to 1 million HeLa cells by laser scanning the entire thermoplasmonic substrate in 3 minutes. Trypsin was used to detach the cells from the substrate for flow cytometry measurements.

After being laser-scanned, each FITC-cargo that was analyzed (FIG. 17) had 6 samples associated with it, including 3 control samples and 3 experimental samples using the conditions shown in the table presented in FIG. 18. The samples were washed with PBS twice (10 mL and 1 mL). Trypsin (2 mL) was added in a dish (35 mm) and incubated (7 min) before neutralizing with pre-warmed cell media (5 mL). Cells were transferred to a tube (15 mL) and centrifuged (125 g, 5 min). The supernatant was removed and cells were re-suspended in PBS (1 mL) and pipetted up and down 30 times before being transferred to a round bottom test tube (5 mL) with a cell strainer snap cap. Flow cytometry measurements were done using BD LSRFortessaSORP™ cell analyzer running BD FACSDiva software version 6.1.3., using the optical setup that is summarized in FIG. 19. Measurements were done following the daily instrument QC, which utilized BD CS&T beads (BD Biosciences, catalog no. 642412) in the following order: B0, GOR0, G1, E1-E3. Appropriate gates were set for each sample using flow cytometry analysis software version FCS Express 5 Research Edition (DeNovo Software™; Glendale, Calif.). 10,000 events were recorded for each sample.

Figure 20A:
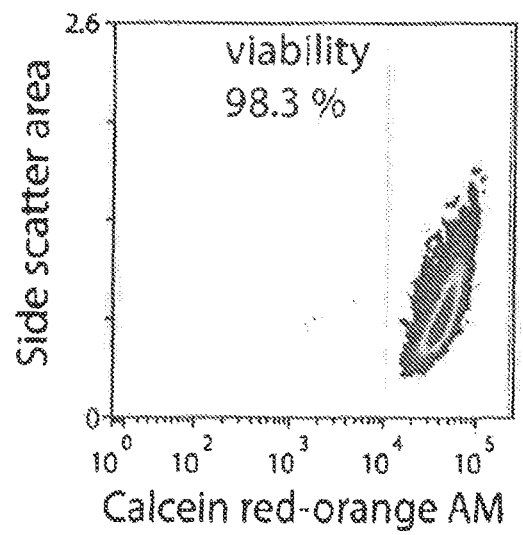
FIG. 20A is a flow cytometry diagram depicting calcein red-orange AM flurorescence as a function of side scatter-area where the experimental sample was not laser scanned.
Figure 20B:
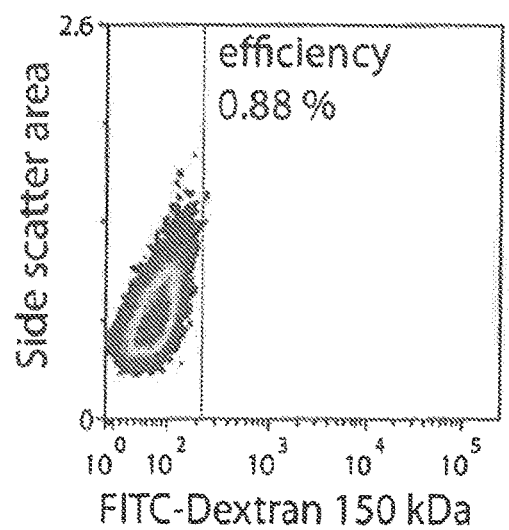
FIG. 20B is a flow cytometry diagram depicting FITC-Dextran 150 kDa fluorescence as a function of side scatter-area where the experimental sample was not laser scanned.
Figure 20C:
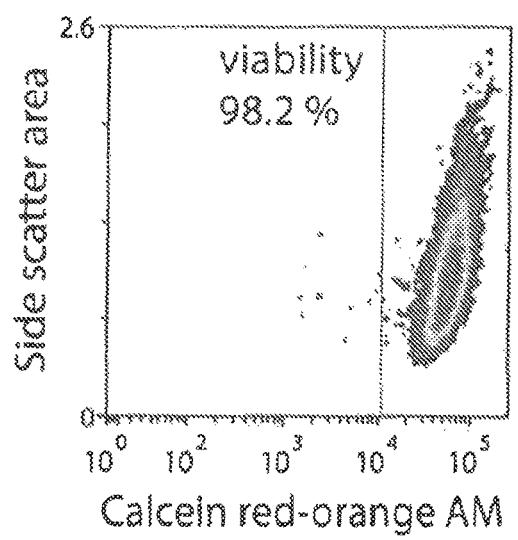
FIG. 20C is a flow cytometry diagram depicting calcein red-orange AM flurorescence as a function of side scatter-area where the experimental sample was laser scanned in accordance with aspects of the present disclosure.
Figure 20D:
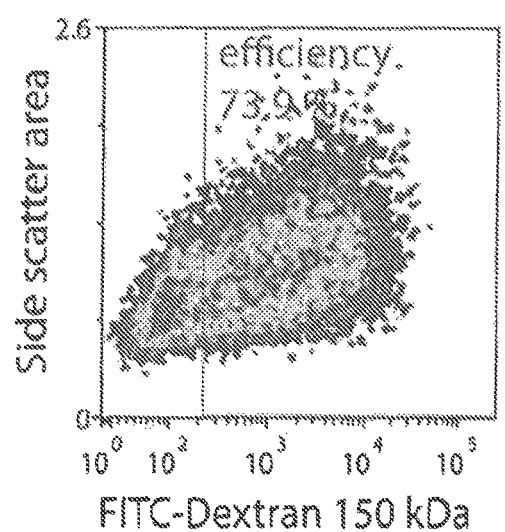
FIG. 20D is a flow cytometry diagram depicting FITC-Dextran 150 kDa flurorescence as a function of side scatter-area where the experimental sample was laser scanned in accordance with aspects of the present disclosure.

FIGS. 20A-D show flow cytometry diagrams from FITC-Dextran 150 kDa experiments that compare viability and delivery efficiency of sample cells that were not laser-scanned (FIGS. 16A-16B) and sample cells that were laser-scanned (FIG. 20C-20D). Both sample cells were initially incubated in a solution containing the cargo to be delivered and then incubated in Calcein AM red-orange for viability indication. For the substrate that was not laser-scanned, the viability is 98.3% and the background signal for delivery is less than 1% (FIG. 20A-20B). For the laser-scanned substrate, the viability is 98.2% and the delivery efficiency is 74% (FIG. 20C-20D).

Figure 20E:
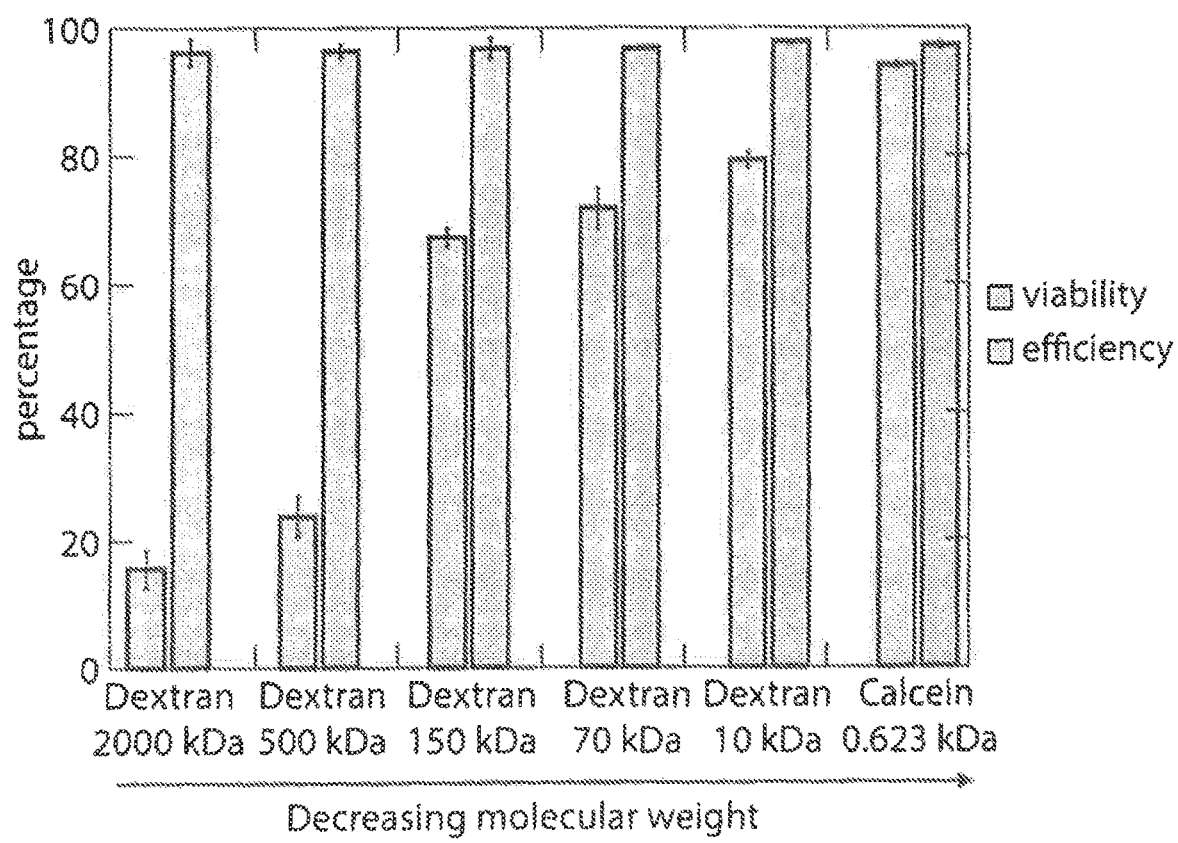
FIG. 20E is a histogram depicting the viability and efficiency for delivery of FITC-cargo ranging in size from 0.623 kDa to 2000 kDa (the data represent mean±SE from n=3 independent experiments) in accordance with aspects of the present disclosure.
Figure 21A:
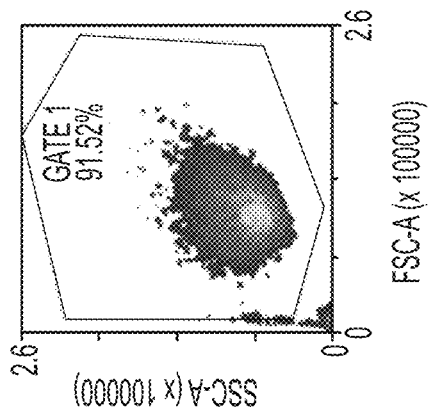
FIG. 21A is a flow cytometry diagram depicting FSC-A as a function of SSC-A for FITC-dextran 150 kDa delivery and flat edge sample in accordance with aspects of the present disclosure.
Figure 21B:
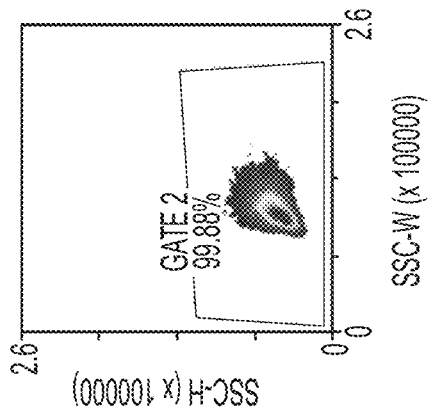
FIG. 21B is a flow cytometry diagram depicting SSC-W as a function of SSH-C for FITC-dextran 150 kDa delivery and flat edge sample in accordance with aspects of the present disclosure.
Figure 21C:
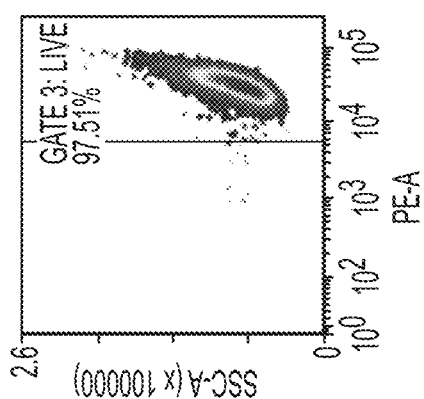
FIG. 21C is a flow cytometry diagram depicting PE-A as a function of SSC-A for FITC-dextran 150 kDa delivery and flat edge sample in accordance with aspects of the present disclosure.
Figure 21D:
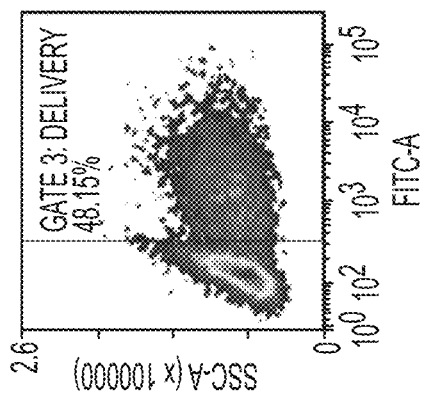
FIG. 21D is a flow cytometry diagram depicting FITC-A as a function of SSC-A for FITC-dextran 150 kDa delivery and flat edge sample in accordance with aspects of the present disclosure.
Figure 21E:
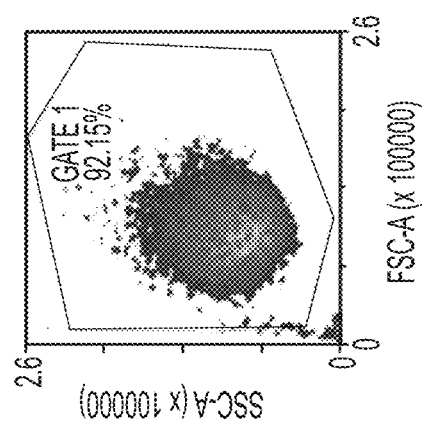
FIG. 21E is a flow cytometry diagram depicting FSC-A as a function of SSC-A for FITC-dextran 150 kDa delivery and no flat edge sample in accordance with aspects of the present disclosure.
Figure 21F:
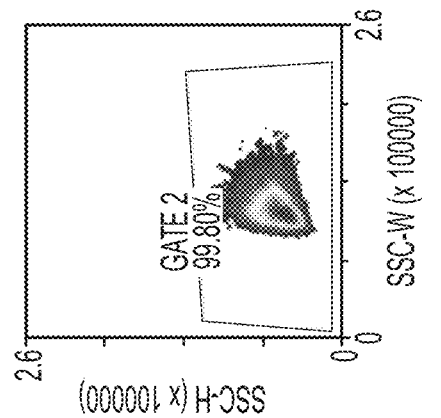
FIG. 21F is a flow cytometry diagram depicting SSC-W as a function of SSH-C for FITC-dextran 150 kDa delivery and no flat edge sample in accordance with aspects of the present disclosure.
Figure 21G:
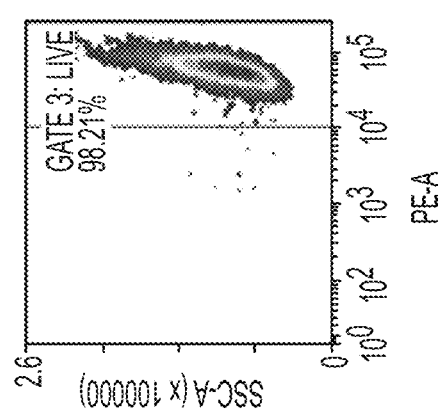
FIG. 21G is a flow cytometry diagram depicting PE-A as a function of SSC-A for FITC-dextran 150 kDa delivery and no flat edge sample in accordance with aspects of the present disclosure.
Figure 21H:
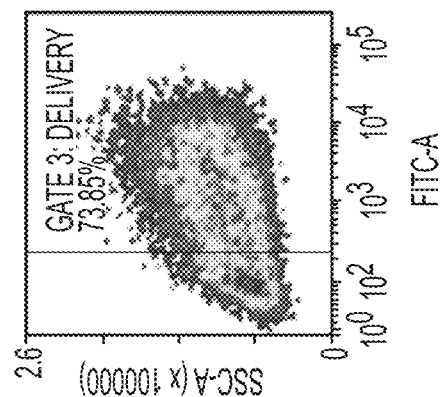
FIG. 21H is a flow cytometry diagram depicting FITC-A as a function of SSC-A for FITC-dextran 150 kDa delivery and no flat edge sample in accordance with aspects of the present disclosure.

FIG. 20E shows an histogram of the viability of cells and delivery efficiency of FITC-cargo ranging in size from 0.623 kDa to 2000 kDa. The data represent mean±SE from n=3 independent experiments. The largest cargo, FITC-Dextran 2000 kDa, was delivered with an efficiency of 16%, and a viability of 97% (FIG. 20E). The largest increase in efficiency was between FITC-Dextran 500 kDa (24%) and FITC-Dextran 150 kDa (68%). Calcein green (0.623 kDa) was delivered at 95% efficiency and 98% viability. The increased efficiency with decreasing cargo size was attributed to faster diffusion for smaller molecules. The delivered cargos match biologically relevant molecules and functional proteins in molecular weight (13 kDa to 150 kDa). Flow cytometry confirms that this technique offers high throughput, high viability, and high efficiency delivery of different cargo sizes.

The data in FIG. 20E are normalized by area of pyramids covering the surface. Regular coverslips were 18 by 18 mm, but only 14 by 14 mm of that area was covered in pyramids, the rest was flat gold, where cells do not have cargo delivered to them when scanned with a laser. Therefore flow cytometry experiments for area normalization were performed from FITC-Dextran 150 kDa samples having flat edge (FIG. 21A-D) and no flat edge (FIG. 21E-H). In the regular samples (with flat edge), an average efficiency of 48.89% for FITC-Dextran 150 kDa was obtained. A triplicate set of experiments with FITC-150 kDa was done on a sample with no flat gold, only pyramids all across on a 14 by 14 mm area, and an efficiency of 67.67% was obtained. The scaling factor of 1.38 (67.67%/48.89%) was used to normalize the efficiency for the different cargos according to surface coverage of the pyramids.

FIGS. 22A-P show presentative flow cytometry data for an entire data set for FITC-Dextran 10 kDa experiments including the data from the control blank sample to set the initial gates (FIGS. 22A-D, Sample ID B0), the control sample to determine the background for green dye and the viability of cells without laser scan (FIG. 22E-H, Sample ID G0R0), the negative control sample to determine the viability (FIG. 22I-L, Sample ID G1), and the experimental samples in triplicate (FIGS. 22M-P, Sample ID E1).

FIGS. 23A-F show the flow cytometry diagrams for different-sized cargos such as the Calcein green 0.623 kDa (FIG. 23A), FITC-Dextran 10 kDa (FIG. 23A), FITC-Dextran 70 kDa (FIG. 23A), FITC-Dextran 150 kDa (FIG. 23A), FITC-Dextran 500 kDa (FIG. 23A), and FITC-Dextran 2000 kDa (FIG. 23A).

Example 11

Thermoplasmonic substrates containing plasmonic micron-sized pyramid arrays were again fabricated using photolithography, anisotropic etching of silicon, metal deposition, and template stripping techniques in a manner discussed above. The thermoplasmonic substrate contained pyramidal structures made of glass coverslip, polymer and a 50 nm gold layer, and having a base length of about 2 µm.

Samples containing HeLa cells and a cargo were seeded on the thermoplasmonic substrates, and the substrates were irradiated with continuous laser radiation using a fiber coupled JDSU diode laser at a wavelength of 980 nm, a power of 500 mW, and an intensity of $10^4$ W/cm$^2$ to deliver the cargo to the cells. More specifically, the samples were positioned in a petri dish and immersed in a solution containing dissolved cargos to be delivered to the cells. The laser beam was focused on the substrate and the petri dish was fixed on an x-y movable stage to scan the sample at a determined speed (which is related to the laser exposure time). The laser parameters were optimized for high-efficiency delivery of small dye molecules like calcein at high-cell viability, using fluorescence microscopy. Alongside small dyes, different-sized fluorescently labeled dextrans were delivered. This method allows for the delivery of molecules in different types of cells. The thermoplasmonic substrate can be reused for repeated high efficiency poration as the substrate undergoes no damage after laser irradiation.

Small dye fluorescent molecules were delivered into cells using continuous wave laser excitation. Intracellular delivery of calcein green (648 Da) was observed. Cell viability was also demonstrated using calcein AM (magenta), which fluoresces only in living cells where the nonfluorescent calcein AM is converted to a fluorescent calcein after acetoxymethyl ester is hydrolyzed by intracellular esterases.

Large areas of thermoplasmonic substrates with seeded cells were scanned while changing the laser intensity in order to change the cell metabolism. The change in cell metabolism of HeLa cells was measured using intense continuous wave laser illumination where the efficiency of FITC-dextran 150 kDa delivery (green) and viability (magenta) was observed for 3 days, i.e., day 0, day 1, and day 2. The columns were scanned from top to bottom while the laser intensity was increased in discrete steps. On day 0, the cells exhibited a decrease in enzymatic activity (as shown by observed magenta) as the laser intensity increased. On day 1, some of the cells recovered. On day 2, some of the cells underwent cell death. Many cells retained the FITC-Dextran 150 kDa that was delivered to them over several days Large dye molecules (FITC-Dextran, 150 kDa) were delivered and retained into HeLa cells for 48 hours after continuous wave laser excitation. Long-term retention of larger dye molecules (FITC-Dextran, 150 k Da) as well as cell division was observed.

Those having ordinary skill in the art will appreciate that various changes can be made to the above embodiments without departing from the scope of the invention. The features disclosed in connection with one embodiment can be utilized in another embodiment. Further, a disclosed numerical range is intended to encompass all numerical values within that range.

What is claimed is:

1. A method of cell processing, comprising:
   disposing a plurality of cells on a substrate having a plurality of projections and an electrically conductive layer at least partially coating said projections,
   exposing the cells to a cargo to be internalized by the cells,
   irradiating the projections with one or more laser pulses having a pulse width in a range of about 5 ns to about 1000 ns so as to facilitate uptake of the cargo by at least a portion of said cells,
   wherein the laser pulses are applied with a fluence in a range of about 40 mJ/cm$^2$ to about 90 mJ/cm$^2$.

2. The method of claim 1, wherein said laser pulses have a pulse width in a range of about 10 ns to about 100 ns.

3. The method of claim 1, wherein said laser pulses have a pulse width in a range of about 20 ns to about 500 ns.

4. The method of claim 1, wherein the laser pulses are applied at a repetition rate of at least about 1 Hz.

5. The method of claim 4, wherein the laser pulses are applied to the cells at a repetition rate in a range of about 0.1 Hz to about 100 GHz.

6. The method of claim 1, wherein said cargo comprises any of a deoxyribonucleic acid (DNA), a ribonucleic acid (RNA), a plasmid, a protein, a dye, a polymer, a quantum dot, a nanoparticle, and a protein complex.

7. The method of claim 6, wherein said protein complex comprises a Cas9-gRNA complex.

8. The method of claim 1, wherein said cargo has a size in a range of about 10 kDa to about 1000 kDa.

9. A method of cell processing, comprising
disposing a plurality of cells on a substrate having a plurality of projections distributed across the substrate and an electrically conductive layer at least partially coating said projections,
exposing the cells to a macromolecular cargo to be internalized by the cells, said cargo having a size ranging from about 10 kDa to about 1000 kDa,
irradiating the projections with one or more laser pulses having a pulse width in range of about 5 ns to about 1000 ns and a fluence sufficient to facilitate uptake of the macromolecular cargo by at least a portion of said cells, and
wherein the laser pulses are applied with a fluence in a range of about 40 mJ/cm$^2$ to about 90 mJ/cm$^2$.

10. The method of claim 9, wherein the laser pulses have a pulse width in a range of about 10 ns to about 1000 ns.

11. The method of claim 9, wherein the projections have a pyramidal shape.

12. The method of claim 11, wherein said pyramidal shape is in the form of a pyramid extending from a base to an apex.

13. A method of delivering a genetic cargo to a cell, comprising:

disposing a plurality of cells on a substrate having a plurality of projections of pyramidal shape, and an electrically conductive layer at least partially coating said projections,
exposing the cells to a genetic cargo to be internalized by the cells, and
irradiating the projections with laser radiation pulses having a pulse width in a range of about 5 ns to about 1000 ns and a fluence in a range of about 40 mJ/cm$^2$ to about 90 mJ/cm$^2$ to induce a transient change in permeability of the cells' membrane to facilitate uptake of the genetic cargo by at least a portion of said cells.

14. The method of claim 13, wherein the genetic cargo comprises a nucleic acid sequence.

15. The method of claim 13, wherein the genetic cargo comprises a Cas9-gRNA complex.

16. The method of claim 13, wherein said pyramidal shape is in the form of a pyramid extending from a base to an apex.

17. The method of claim 1, wherein said plurality of projections have a pyramidal shape.

18. The method of claim 1, wherein said plurality of pyramidal projections have a height in a range of about 0.1 μm to about 20 μm.

19. The method of claim 1, wherein said plurality of pyramidal projections have a height in a range of about 1 μm to about 10 μm.

20. The method of claim 9, wherein said plurality of projections is distributed across the substrate as a regular array.

* * * * *